(12) United States Patent
Stefanchik et al.

(10) Patent No.: US 7,803,137 B2
(45) Date of Patent: Sep. 28, 2010

(54) INTUBATION SYSTEM FOR USE WITH AN ENDOSCOPE

(75) Inventors: David Stefanchik, Morrow, OH (US);
James T. Spivey, Loveland, OH (US);
Jesse J. Kuhns, Cincinnati, OH (US);
Omar Vakharia, Mason, OH (US); Rick D. Applegate, Florence, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1154 days.

(21) Appl. No.: 11/386,584

(22) Filed: Mar. 22, 2006

(65) Prior Publication Data
US 2007/0225728 A1 Sep. 27, 2007

(51) Int. Cl.
*A61B 1/00* (2006.01)
(52) U.S. Cl. ...................................................... 604/174
(58) Field of Classification Search .................. 604/174, 604/106; 600/104, 114, 120, 123, 125, 129, 600/133; 128/207.29
See application file for complete search history.

(56) References Cited

U.S. PATENT DOCUMENTS

| | | | |
|---|---|---|---|
| 2,649,092 A | 8/1953 | Wallace | |
| 2,830,361 A | 4/1958 | Bruner | |
| 3,490,457 A | 1/1970 | Petersen | |
| 3,955,578 A | 5/1976 | Chamness et al. | |
| 4,069,826 A | 1/1978 | Sessions et al. | |
| 4,326,530 A | 4/1982 | Fleury, Jr. | |
| 4,393,873 A | 7/1983 | Nawash et al. | |
| 4,627,838 A | 12/1986 | Cross et al. | |
| 4,758,219 A | 7/1988 | Sacks et al. | |
| 4,826,481 A | 5/1989 | Sacks et al. | |
| 4,921,481 A | 5/1990 | Danis et al. | |
| 5,073,166 A | 12/1991 | Parks et al. | |
| 5,080,650 A | 1/1992 | Hirsch et al. | |
| 5,112,310 A | 5/1992 | Grobe | |
| 5,201,741 A | 4/1993 | Dulebohn | |
| 5,203,773 A | 4/1993 | Green | |
| 5,242,389 A | 9/1993 | Schrader et al. | |
| 5,248,302 A | 9/1993 | Patrick et al. | |

(Continued)

FOREIGN PATENT DOCUMENTS

EP 0256546 2/1988

(Continued)

OTHER PUBLICATIONS

Examination Report, European Application No. 07251197.5 (Jul. 17, 2009).

(Continued)

*Primary Examiner*—Kevin T Truong
(74) *Attorney, Agent, or Firm*—Victor C. Moreno

(57) ABSTRACT

An intubation system is provided for use with an endoscope. The intubation system includes a guide apparatus having a track that is adapted to be associated with the endoscope such that bending of the track is substantially decoupled from bending of the endoscope. The intubation system also includes a positioning device having a first coupling member on the distal end and an intubation device having a second coupling member on the proximal end. The intubation device and the positioning device each include a mating member that is adapted to slidingly engage the track external of the endoscope, whereby the first and second coupling members may be releasably attached together.

17 Claims, 20 Drawing Sheets

U.S. PATENT DOCUMENTS

| | | | |
|---|---|---|---|
| 5,279,542 A | 1/1994 | Wilk | |
| 5,290,294 A | 3/1994 | Cox et al. | |
| 5,309,346 A | 5/1994 | Gyugyi | |
| 5,334,167 A | 8/1994 | Cocanower | |
| 5,356,382 A | 10/1994 | Picha et al. | |
| 5,431,640 A | 7/1995 | Gabriel | |
| 5,462,553 A | 10/1995 | Dolgin | |
| 5,501,692 A | 3/1996 | Riza | |
| 5,522,819 A | 6/1996 | Graves et al. | |
| 5,643,175 A * | 7/1997 | Adair | 600/133 |
| 5,665,064 A | 9/1997 | Bodicky et al. | |
| 5,752,961 A | 5/1998 | Hill | |
| 6,049,960 A | 4/2000 | Pilling et al. | |
| 6,071,282 A | 6/2000 | Fleischman | |
| 6,077,250 A * | 6/2000 | Snow et al. | 604/174 |
| 6,224,611 B1 | 5/2001 | Ouchi | |
| 6,364,858 B1 | 4/2002 | Picha | |
| 6,444,913 B1 | 9/2002 | Kao | |
| 6,547,761 B2 | 4/2003 | Liu | |
| 6,569,085 B2 | 5/2003 | Kortenbach et al. | |
| 6,695,832 B2 | 2/2004 | Schon et al. | |
| 6,730,097 B2 * | 5/2004 | Dennis | 606/113 |
| 6,786,864 B2 | 9/2004 | Matsuura et al. | |
| 6,878,106 B1 * | 4/2005 | Herrmann | 600/104 |
| 6,893,418 B2 * | 5/2005 | Liu | 604/106 |
| 6,910,581 B2 | 6/2005 | McMichael et al. | |
| 7,127,295 B2 | 10/2006 | Evans | |
| 2002/0002361 A1 | 1/2002 | Fanelli et al. | |
| 2002/0087183 A1 | 7/2002 | Boyd et al. | |
| 2002/0107506 A1 | 8/2002 | McGuckin et al. | |
| 2002/0107530 A1 | 8/2002 | Sauer et al. | |
| 2003/0130564 A1 | 7/2003 | Martone et al. | |
| 2004/0059293 A1 | 3/2004 | Chu et al. | |
| 2004/0064017 A1 | 4/2004 | Cappiello et al. | |
| 2004/0230095 A1 | 11/2004 | Stefanchik et al. | |
| 2004/0230096 A1 | 11/2004 | Stefanchik et al. | |
| 2005/0085808 A1 | 4/2005 | Nakao | |
| 2005/0125005 A1 | 6/2005 | Fujikura | |
| 2005/0209609 A1 | 9/2005 | Wallace | |
| 2005/0234297 A1 | 10/2005 | Devierre et al. | |
| 2005/0256374 A1 | 11/2005 | Long et al. | |
| 2005/0261674 A1 * | 11/2005 | Nobis et al. | 606/45 |
| 2006/0100475 A1 | 5/2006 | White et al. | |

FOREIGN PATENT DOCUMENTS

| | | |
|---|---|---|
| EP | 0742708 | 4/2002 |
| EP | 1477104 | 11/2004 |
| EP | 1721562 | 11/2006 |
| EP | 1721564 | 11/2006 |
| EP | 1721567 | 11/2006 |
| WO | WO 92/10222 | 6/1992 |
| WO | WO 95/20936 | 8/1995 |
| WO | 98/19608 | 5/1998 |
| WO | 2004/021867 | 3/2004 |
| WO | 2005/074819 | 8/2005 |

OTHER PUBLICATIONS

European Search Report, European Application No. 07251185.0 (5 pages) (Dec. 11, 2009).

* cited by examiner

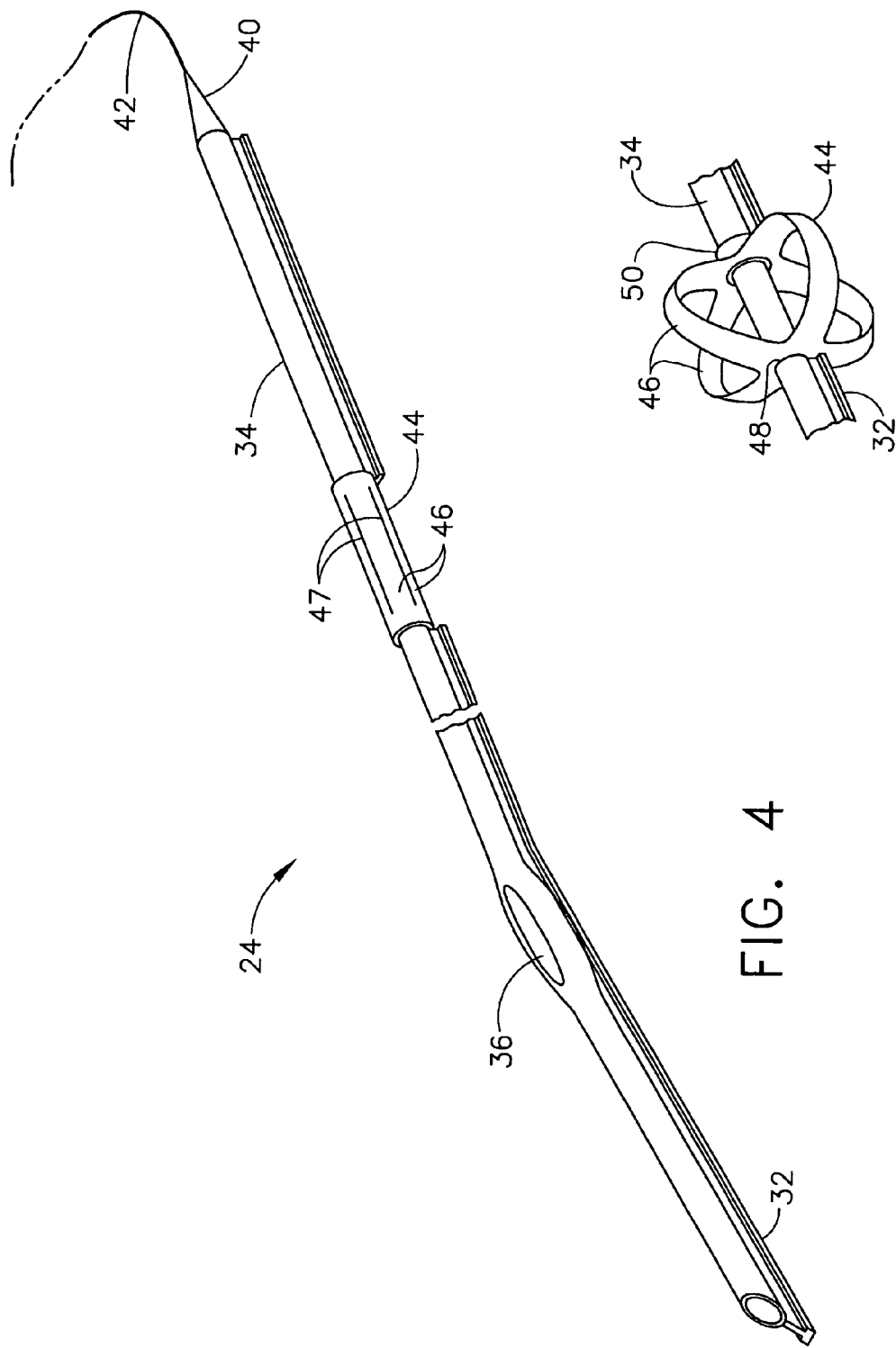

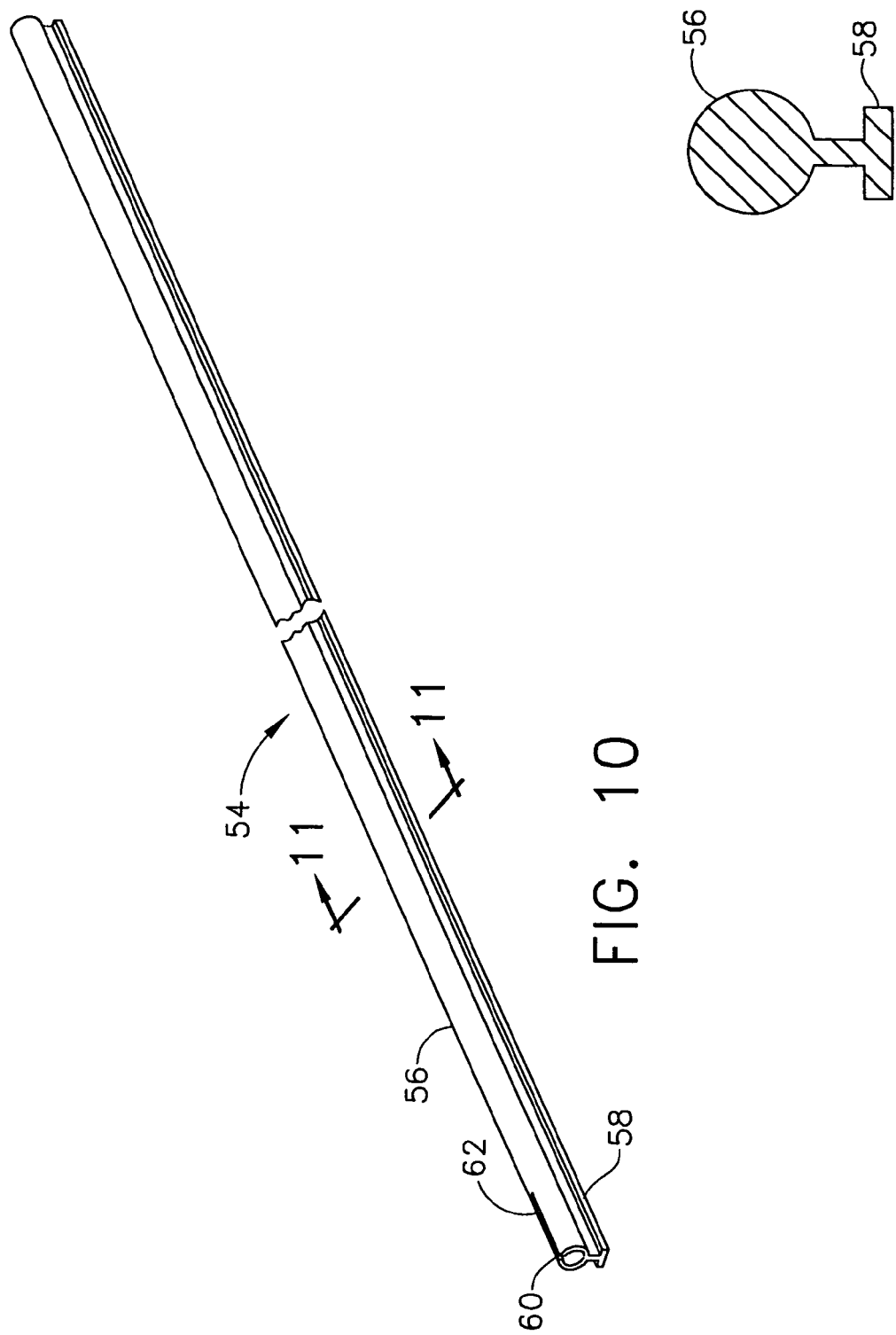

INTUBATION SYSTEM FOR USE WITH AN ENDOSCOPE

FIELD OF THE INVENTION

This application is related to the following patent applications, the entire contents of which are incorporated herein by reference:

U.S. Ser. No. 10/440,957 (published as US 2004/0230095), filed May 12, 2003;

U.S. Ser. No. 10/440,660 (published as US 2004/0230096), filed May 12, 2003;

U.S. Ser. No. 10/440,956 (published US 2004/0230097), filed May 16, 2003; and

U.S. Ser. No. 11/128,108 titled "Medical Instrument Having a Guidewire and an Add-to Catheter" filed May 12, 2005 in the name of Long et al.

The present application generally relates to endoscopic medical devices and methods and, more particularly, to devices and methods useful in flexible endoscopic medical procedures.

BACKGROUND OF THE INVENTION

Physicians perform many medical procedures using flexible endoscopes inserted through natural body openings in the patient's body. Flexible endoscopes typically have a flexible shaft with an articulating distal end that the physician may control using actuators on the proximal end of the endoscope. Many flexible endoscopes, including gastroscopes and colonoscopes, have integral working channels (also called biopsy channels or accessory channels) that provide access to the tissue of interest with diagnostic and therapeutic devices. The diameter of the working channel may range from 1 to 4 millimeters, depending on the size and type of endoscope.

The diameter of the working channel limits the medical devices that the physician can use through the endoscope, and the size of objects (blood clots, biopsy samples, etc.) that the physician can remove from the patient's body. In addition, the physician may be limited to using a single device at a time when using a conventional endoscope having only one working channel, sometimes requiring numerous, time-consuming insertions/removals of the devices during a procedure. Certain specialized endoscopes are available that have extra large working channels or a pair of working channels. However, such specialized endoscopes may be more expensive, larger in diameter, stiffer, and more difficult to intubate than standard endoscopes.

One example of a medical procedure involving the upper gastrointestinal (GI) tract is placement of an enteral feeding tube into the small intestine of a patient. Such a procedure is generally known as a percutaneous endoscopic gastrojejunostomy (PEGJ) procedure. In a gastroscope-assisted PEGJ, the physician may insert and remove a gastroscope into the upper GI tract a number of times in order to place the distal end of the feeding tube in the jejunum under visualization of the endoscope and to secure the proximal portion of the feeding tube to the abdominal and gastric walls. These repeated insertions/removals are time-consuming and may result in significant trauma to tissue and post-procedural soreness in the upper GI tract of the patient.

The same issues may also be associated with current intubating procedures in the lower GI tract via the anus of the patient. For example, sometimes to improve patient comfort it is necessary for the physician to place a colonic decompression tube into the colon of the patient to release gas produced by the body. However, current techniques of navigating a flexible tube through the flexures of the colon may be time-consuming, traumatic to tissue, and painful to the patient.

Accordingly, there is a need for improved devices and methods that are adapted for use with a flexible endoscope, and that provide improved endoscopic access to the tissue of interest with medical devices for numerous medical purposes, including performing diagnostic and therapeutic procedures, supplying fluid nutrients into the gastrointestinal tract, removing diseased tissue and releasing gas.

SUMMARY OF THE INVENTION

An intubation system is provided for use with an endoscope. The intubation system includes a guide apparatus having a track that is adapted to be associated with the endoscope such that bending of the track is substantially decoupled from bending of the endoscope. The intubation system also includes a positioning device having a first coupling member on the distal end and an intubation device having a second coupling member on the proximal end. The intubation device and the positioning device each include a mating member that is adapted to slidingly engage the track external of the endoscope, whereby the first and second coupling members may be releasably attached together.

A method of using an intubation system with an endoscope is also provided. The method includes providing an intubation system as described in the previous paragraph. The method further includes assembling the guide apparatus onto the endoscope, inserting the guide apparatus and endoscope into an endoscopic opening in the patient, slidably engaging the intubation device to the guide apparatus, releasably attaching the first coupling member of the positioning device to the second coupling member of the intubation device, slidably engaging the positioning device to the guide apparatus, and applying a force to the positioning device to move the intubation device along the guide apparatus.

Other aspects, variations, and embodiments of the intubation system and method will become apparent from the following description, the accompanying drawings, and the appended claims.

BRIEF DESCRIPTION OF THE FIGURES

FIG. 4 is an isometric view of an intubation device for use with the guide apparatus shown in FIG. 1, wherein the intubation device includes a first version of a tissue bolster, which is shown in a collapsed configuration;

FIG. 5 is an isometric view of the tissue bolster of FIG. 4 shown in an expanded configuration;

FIG. 10 is an isometric view of a positioning device for use with the guide apparatus of FIG. 1;

FIG. 11 is a cross-sectional view taken at line 11-11 of FIG. 10 of the positioning device;

FIGS. 15 through 20 are illustrations of an endoscope assembled with the guide apparatus of FIG. 1 and inserted into the upper gastrointestinal tract of a patient, wherein FIG. 15 shows a needle and a cannula penetrated through a transilluminated portion of the gastric and abdominal walls;

FIG. 16 shows the distal end of the endoscope passing through a wire loop that was introduced into the stomach via the cannula placed through the gastric and abdominal walls;

FIG. 17 shows the intubation device of FIG. 4 being advanced by the positioning device of FIG. 10 along the guide apparatus so that the distal end of the intubation device is positioned inside the jejunum within the visual range of the endoscope;

FIG. 18 shows the wire loop snaring a trailing filament attached to the proximal end of the intubation device, which has been pushed by the positioning device off of the guide apparatus and into the inside of the stomach while within the visual range of the endoscope;

FIG. 19 shows the trailing filament and the proximal end of the intubation device externalized through the gastric and abdominal walls;

FIG. 20 shows the tissue bolster bearing against the inside of the gastric wall, changed to the expanded configuration and secured in position by a surgical clamp attached to the externalized portion of the intubation device, and showing a Y-fitting attached to the proximal end of the intubation device and the endoscope being removed from the patient;

FIGS. 21 through 23 illustrate steps for using a snaring device with a percutaneous cannula positioned through the abdominal and gastric walls of a patient, wherein FIG. 21 shows a distal portion of a flexible member of the snaring device extending into the stomach while the flexible member is in a straight configuration;

FIG. 22 shows tension being applied to a tensioning element as the flexible member is held, and the distal portion of the flexible member of the snaring device formed into a looped configuration and encircling the trailing filament of the intubation device;

FIG. 23 shows the tension released from the tensioning element and the flexible member in a straight configuration, with the filament snared between the flexible member and the tensioning element;

DETAILED DESCRIPTION OF THE INVENTION

Figure 1:
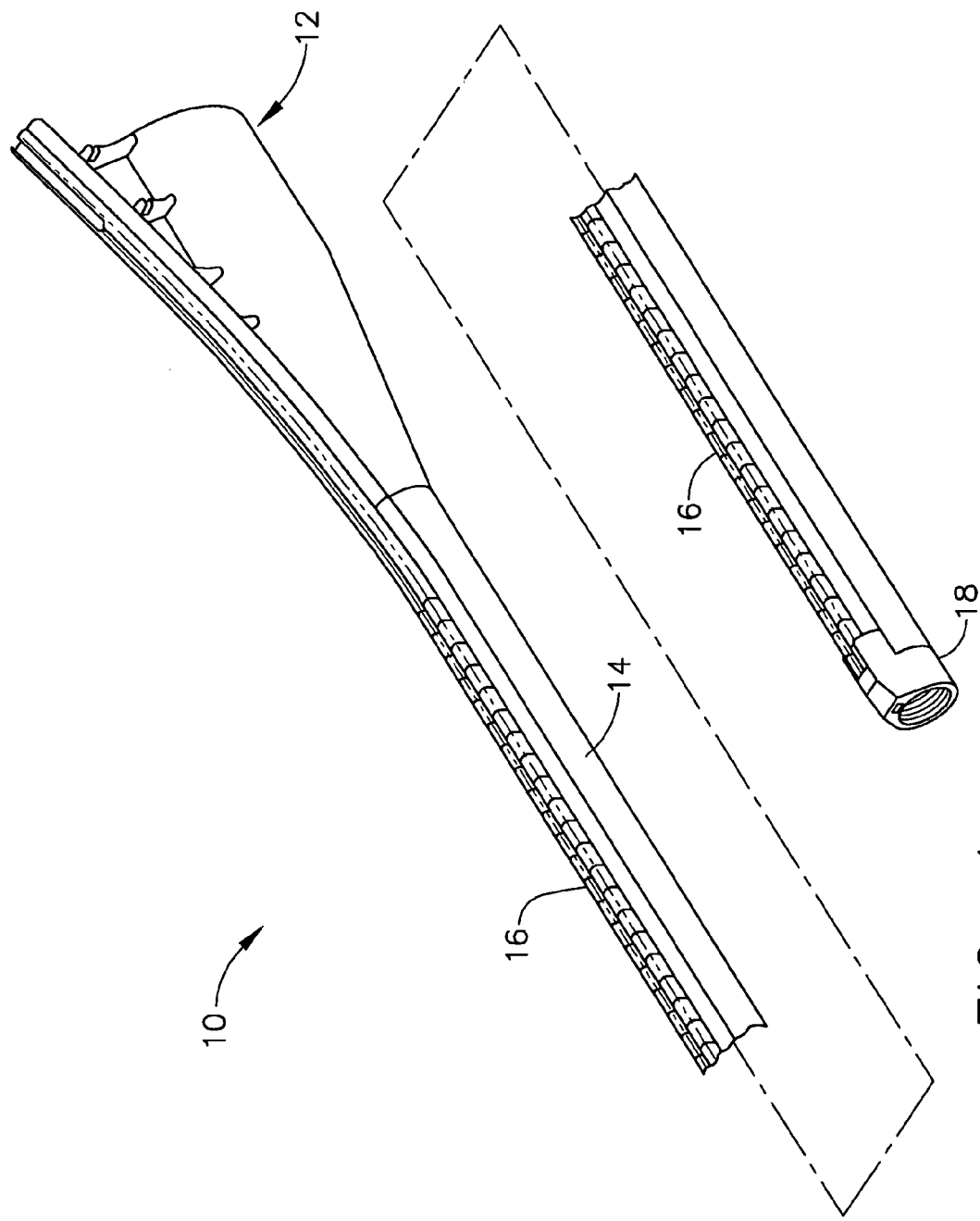
FIG. 1 is an isometric view of a guide apparatus for use with an endoscope.

FIG. 1 is an isometric view of a guide apparatus (also referred to as a medical apparatus) generally designated 10. The earlier referenced U.S. patent application, Ser. No. 11/128,108 includes a detailed description of apparatus 10. Generally, however, apparatus 10 may include a handle 12, a flexible sheath 14 extending from handle 12, a flexible track 16 attached to sheath 14, and an endcap 18 attached to the distal end of sheath 14. Handle 12 and sheath 14 may be sized to receive a flexible endoscope. Sheath 14 may be formed from a thin polymeric film such as polyethylene or polypropylene, and be sufficiently long to cover the entire endoscopic portion of the endoscope. Track 16 may be formed from a continuous piece of a flexible, low-friction polymer such as an extruded polypropylene.

Many types of endoscopes may be used with guide apparatus 10, including a conventional, flexible gastroscope, colonoscope or pediatric colonoscope having an articulating distal section. Although such endoscopes typically include a working channel, it is also possible to use apparatus 10 with endoscopes that do not have a working channel. Apparatus 10 is removable from the endoscope and disposable, and allows the use of at least one flexible accessory device that is too large to pass through the working channel (if provided) of the endoscope. The accessory may be adapted to slide on the track of the apparatus external of the endoscope, such that bending of the track is substantially decoupled from bending of the endoscope. In addition, the track may be supported relative to the endoscope, such that the track is capable of moving circumferentially with respect to the endoscope.

Figure 2:
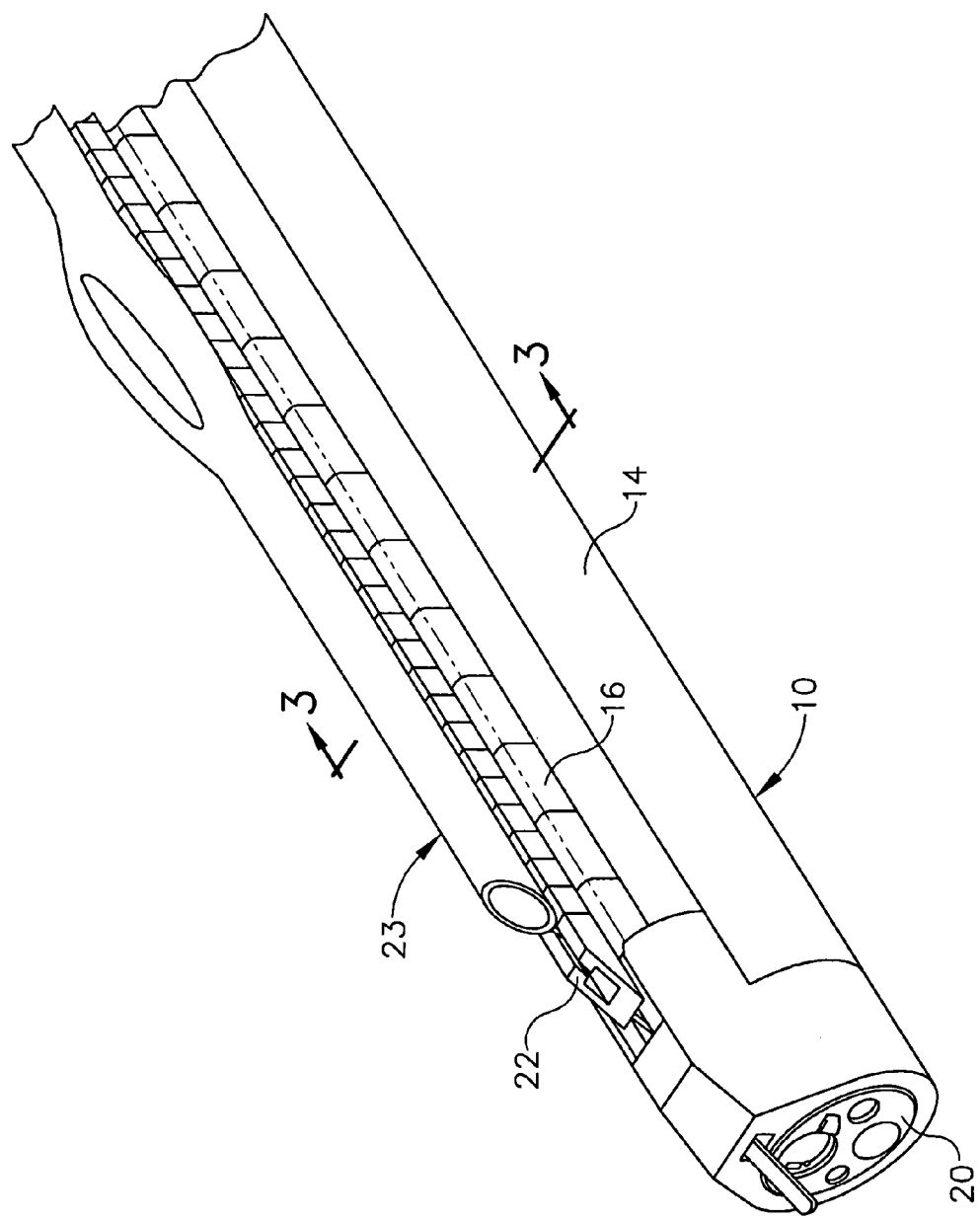
FIG. 2 is an isometric view of the distal portion of the guide apparatus of FIG. 1 assembled onto an endoscope, and an accessory in sliding engagement with the guide apparatus.

FIG. 2 is an isometric view of the distal portion of apparatus 10 assembled onto an endoscope 20. Apparatus 10 may include a carrier 22 which is adapted to slidably engage track 16. Carrier 22 may be unitarily formed from an extruded, low-friction polymer such as PTFE and may have a length that is at least as long as track 16. An accessory 23 may be adapted to slidingly engage carrier 22, as shown. Accessory 23 may be adapted for supplying fluid nutrients to the body, providing access to a tissue of interest for diagnostic and therapeutic medical devices, for evacuating or releasing a gas or other fluid from the body, or for any of a number of other medical purposes.

Figure 3:
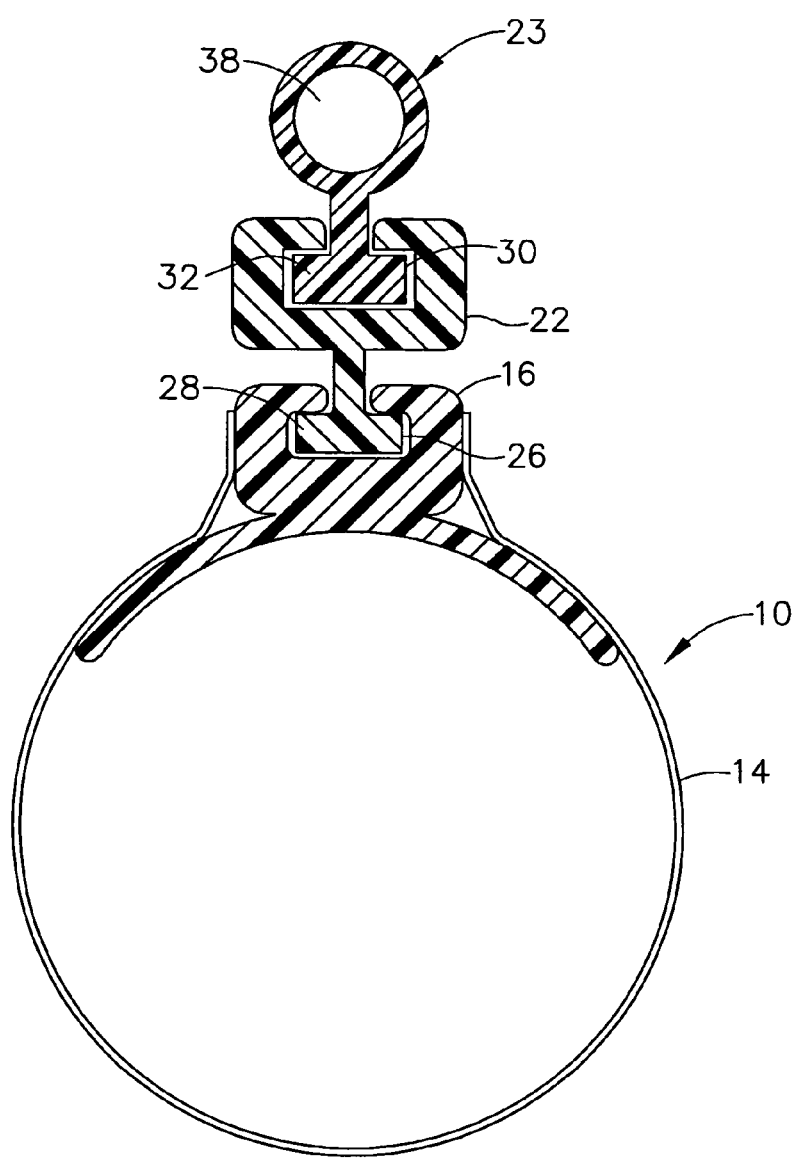
FIG. 3 is a cross-sectional view taken at line 3-3 of FIG. 2 of the accessory in sliding engagement with a carrier, and the carrier in sliding engagement with a track of the guide apparatus, wherein the endoscope has been removed for clarity.

FIG. 3 is a cross-sectional view taken at line 3-3 of FIG. 2 of accessory 23 slidingly engaged to apparatus 10. (A cross-sectional view of endoscope 20 is not shown in FIG. 3 for clarity. It should be noted that since sheath 14 may be formed from a thin polymeric film, sheath 14 would not necessarily maintain a circular configuration as shown in FIG. 3 without endoscope 20 positioned inside it.) The cross-sectional profile of track 16 may have a C-shape that defines a T-shaped, track channel 26. Carrier 22 may include a T-shaped rail 28 that may slidably engage track channel 26. Carrier 22 may also include a T-shaped, carrier channel 30 as shown in FIG. 3 for sliding engagement with a T-shaped accessory rail 32 (also referred to as a mating member) of accessory 23.

FIG. 4 is an isometric view of an intubation device 24, which may be used with guide apparatus 10 of FIG. 1. Intubation device 24 may be used as an enteral feeding tube for placement in a patient according to a percutaneous endoscopic gastrojejunostomy (PEGJ) procedure to be described herein. The distal end of intubation device 24 may be positioned in the jejunum. Intubation device 24 may extend proximally through the proximal portion of the jejunum and duodenum of the small intestine, into the stomach and pass through the gastric and abdominal walls so that the proximal end may be accessed for administering nutrients or other substances.

Intubation device 24 may include an elongate tube 34 defining a passageway 38 (see FIG. 3) therethrough that is in fluid communication with a distal port 36. Distal port 36 may be positioned a distance of approximately 5 to 15 centimeters from the distal end of intubation device 24, although this distance may vary. Except for the addition of rail 32, the distal portion of intubation device 24 may be very similar to the distal portion of numerous, commercially available feeding tubes, such as a 140 centimeter long, 10 French, Dobb-Hoff type feeding tube available from Viasys Healthcare, Inc. Rail 32 and tube 34 may be formed separately then bonded together, or unitarily formed from an extruded polymer such as a medical grade polyurethane. The length of tube 34 may be approximately in the range of 50 to 100 centimeters. Rail 32 may extend along substantially the entire length of tube 34, or along one or more portions of tube 34. Rail 32 may be adapted to be releasably engaged with carrier 22, as shown in FIG. 3. Optionally, rail 32 may also be adapted to be releasably engaged with track 16. A medical lubricant such as K-Y Jelly™ (Johnson and Johnson Corp.) may be applied to the interface between rail 32 and its mating component, carrier 22 or track 16, to reduce the force required to move intubation device 24 along guide apparatus 10.

The proximal and distal ends of intubation device 24 may be closed. The distal end of intubation device 24 may be tapered to facilitate advancement through the upper GI tract.

As shown in FIG. 4, the proximal end of intubation device 24 may include a coupling member 40 having a conically tapered shape, although other shapes are possible. Coupling member 40 may be adapted to couple together with a positioning device, which is shown in FIG. 10. A filament 42 may be attached to the distal end of intubation device 24. The filament may be formed from a conventional surgical suture material, a thin metallic wire, a polymeric cord or a natural fiber, for example, and be approximately 20-80 centimeters long.

A conventional enteral feeding tube is typically provided with a tissue stop or bumper attached near the proximal end to bear against the inner stomach wall when the proximal end of the tube is externalized and secured to the abdominal wall. As shown in FIGS. 4-9, intubation device 24 may include an improved tissue stop, a tissue bolster 44, that has a minimal size when introduced into the upper GI tract and that deploys or expands automatically when the proximal end of intubation device 24 is secured to the abdominal wall. Providing the collapsible, tissue bolster 44 enables insertion of intubation device 24 while the endoscope is positioned in the upper GI tract, thereby minimizing trauma to the delicate lining of the upper GI tract while providing visualization inside the stomach and avoiding repeated insertions/removals of the endoscope as required in conventional PEGJ procedures.

In FIG. 4, a first version of tissue bolster 44 is shown positioned on the proximal portion of intubation device 24 and in a collapsed configuration. Bolster 44 may be positioned, for example, approximately 10 to 15 centimeters from the proximal end of intubation device 24. When the physician pulls the proximal end of intubation device 24 through the abdominal wall, as shown in FIGS. 6 and 7, bolster 44 bears against the inner stomach wall and automatically expands to an expanded configuration, as shown in FIG. 5.

Tissue bolster 44 may be formed from a biocompatible polymer, such as a short length of an extruded polyurethane tube that fits loosely over tube 34 of intubation device 24. A portion of rail 32 may be removed from tube 34 at the location of bolster 44. A first end 48 of bolster 44 may be attached to tube 34, such as with an adhesive, and a second end 50 may be permitted to slide freely over tube 34. Bolster 44 may include a plurality of arms 46 that may be formed by a plurality of parallel slits 47 in the material of bolster 44 between first end 48 and second end 50. When first and second ends, 48 and 50, are urged towards each other as shown in FIG. 5, arms 46 flex radially outward, thereby forming a broad surface that may bear against the stomach wall when deployed. When secured, tissue bolster 44 may also function to seal against the incision in the gastric wall to prevent leakage of gastric fluids into the abdominal cavity.

Figure 6:
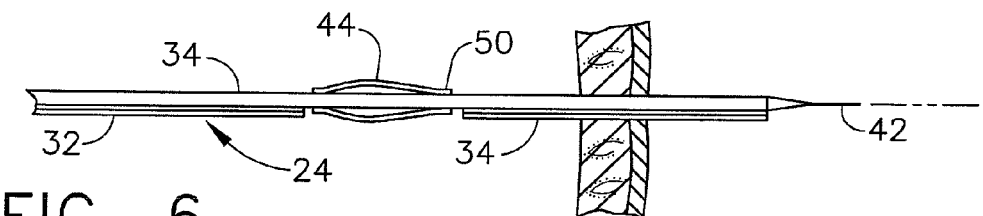
FIG. 6 is a side view of the proximal portion of the intubation device shown in FIG. 4 being positioned through the body wall, showing the tissue bolster in a collapsed configuration.
Figure 7:
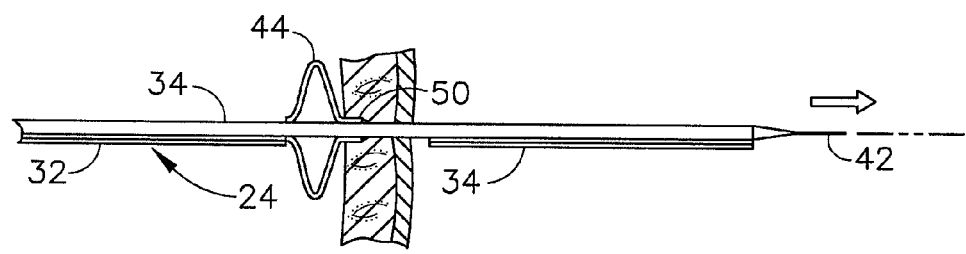
FIG. 7 is a side view of the proximal portion of the intubation device shown in FIG. 6, showing the tissue bolster bearing against the body wall and changed to an expanded configuration.

FIG. 6 shows the first version of tissue bolster 44 in the collapsed configuration as the proximal portion of intubation device 24 is passed through an incision in the gastric and abdominal walls. FIG. 7 shows tissue bolster 44 of FIG. 6 in the expanded configuration and bearing against the inner gastric wall. When the patient no longer needs tube 34 for enteral feeding, the physician may pull on the external portion of tube 34 to pull intubation device 24 out through the body wall incision, as is the current practice using conventional enteral feeding tubes with non-collapsible tissue bolsters.

Figure 8:
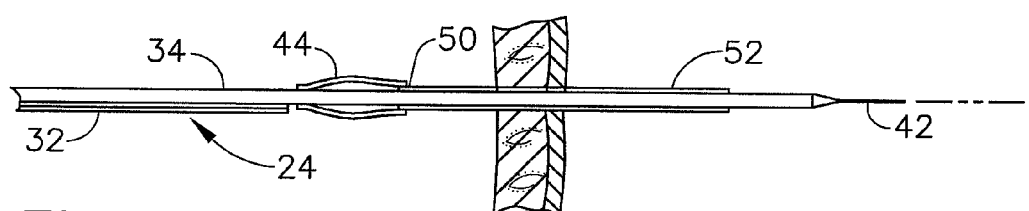
FIG. 8 is a side view of the proximal portion of the intubation device being positioned through the body wall, wherein the intubation devices includes a second version of a tissue bolster, shown in a collapsed configuration.
Figure 9A:
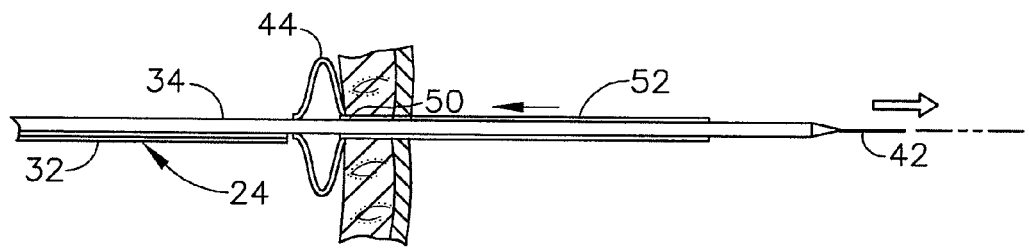
FIG. 9A is a side view of the proximal portion of the intubation device shown in FIG. 8, showing the tissue bolster bearing against the body wall and changed to an expanded configuration.

FIG. 8 shows a second version of tissue bolster 44 in a collapsed configuration and including a bolster extension 52 attached to second end 50 of bolster 44. Extension 52 may be a thin wall, polymeric tube adapted to slide freely over tube 34. FIG. 9A shows second version of bolster 44 in an expanded configuration and bearing against the inner gastric wall. Bolster 44 automatically deploys to the expanded configuration as filament 42 is pulled and bolster 44 bears against the inner gastric wall, which in turn bears against the inner abdominal wall. Extension 52 provides an external hold to manipulate bolster 44 between the expanded and collapsed configurations, thereby facilitating positioning and/or the easy removal of intubation device 24 from the patient. Extension 52 may also be a short length of filament attached to end 50, or any one of numerous other slender structures that may be passed through the abdominal incision alongside of tube 34.

Figure 9B:
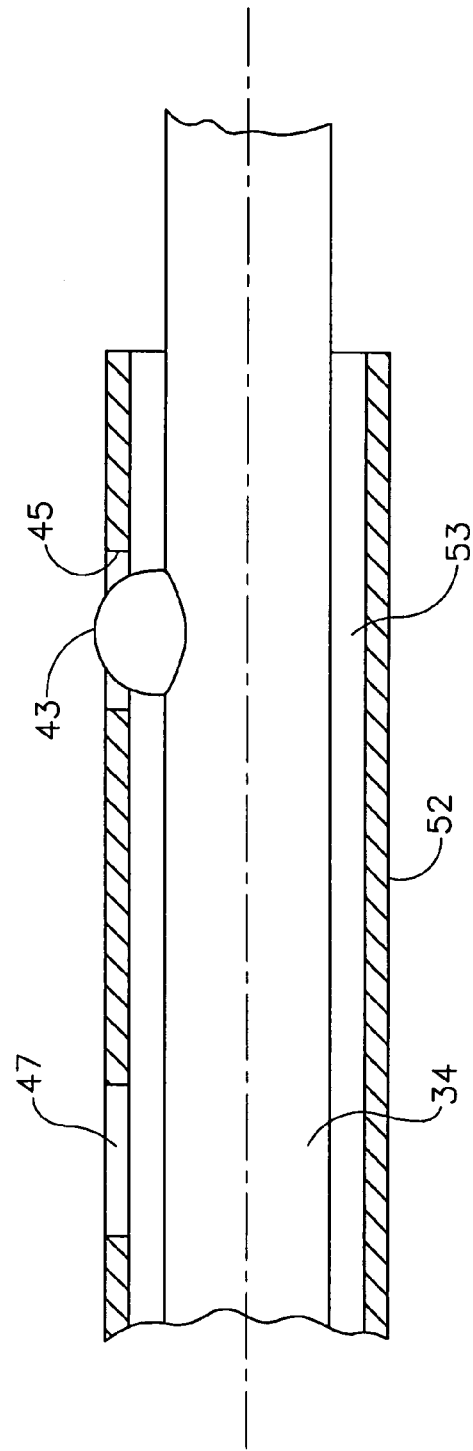
FIG. 9B is a detailed side view of a proximal portion of the intubation device shown in FIG. 9A, showing a releasable locking element engaged in a detent aperture to hold the tissue bolster in the collapsed configuration.

Optionally, the outer diameter of tube 34 may be approximately 1.0 to 3.0 millimeters smaller than the inner diameter of extension 52 so that a clearance between tube 34 and extension 52 defines a passageway 53, as shown in a detailed view of tube 34 and extension 52 in FIG. 9B. A physician may administer a fluid such as a drug solution, for example, into the stomach or place the proximal end of extension 52 into fluid communication with an aspiration device to remove gastric fluids from the stomach.

FIG. 9B also shows a releasable locking element 43 that is releasably engageable with a first detent aperture 47 and a second detent aperture 45. A physician may hold tube 34 while moving extension 52 longitudinally between the first and second detent apertures 47, 45, in order to releasably lock tissue bolster 44 in the expanded and collapsed configurations, respectively. The position of releasable locking element 43 is not restricted to the proximal portion of tube 34 extending out of the patient's body, but may also be provided on the portion of tube 34 near tissue bolster 44 inside the body. A similar locking element, including a latch, detent, or the like, may also be provided on the first version of tissue bolster 44 shown in FIG. 6 so that tissue bolster 44 locks into the expanded configuration when pulled against the body wall. Tissue bolster 44 would remain in the expanded configuration without needing to secure tube 34 to the body wall, as described for the first version of tissue bolster 44.

As noted earlier, intubation device 24 may include a coupling member 40 on the proximal end for coupling with another accessory. FIG. 10 is an isometric view of such an accessory, a positioning device 54, for use with guide apparatus 10 shown in FIG. 1. A physician may use positioning device 54 to remotely move intubation device 24 in the longitudinal direction along track 16 of guide apparatus 10 or along carrier 22, which is attached to track 16. Positioning device 54 basically provides a physician with the ability to push intubation device 24 in the distal direction and to pull intubation device 24 in the proximal direction when the proximal end of intubation device 24 is inside the patient's body and not directly accessible by the physician. Another important function of positioning device 54 is to hold intubation device 24 stationary relative to the patient so that the endoscope and guide apparatus 10 may be withdrawn in the proximal direction, and perhaps removed from the patient, without altering the position of the distal end of the intubation device.

Positioning device 54 includes an elongated body 56 having a rail 58 (also referred to as a mating part) attached thereto along substantially the entire length of body 56. Rail 58 may be adapted to slidingly engage with carrier channel 30 or with track channel 26 (see FIG. 3). Body 56 and rail 58 may be unitarily formed from a continuous piece of a low-friction, polymeric material such as an extruded polyethylene or PTFE. The length of positioning device 54 may be at least as long as track 16 of apparatus 10, such as for example, approximately in the range of 100 to 200 centimeters. Positioning device 54 may be flexible enough to be advanced and retracted along apparatus 10 in the upper GI tract, but relatively stiff in comparison to intubation device 24. The cross-sectional profile of body 56 of positioning device 54 may have any one of numerous geometric shapes, including a circular shape as shown in FIG. 11. Body 56 may also include a channel extending at least partially therethrough (not shown), which may be used, for example, to administer or evacuate a fluid, to provide access into the upper GI tract for another device or for other purposes.

Figure 12:
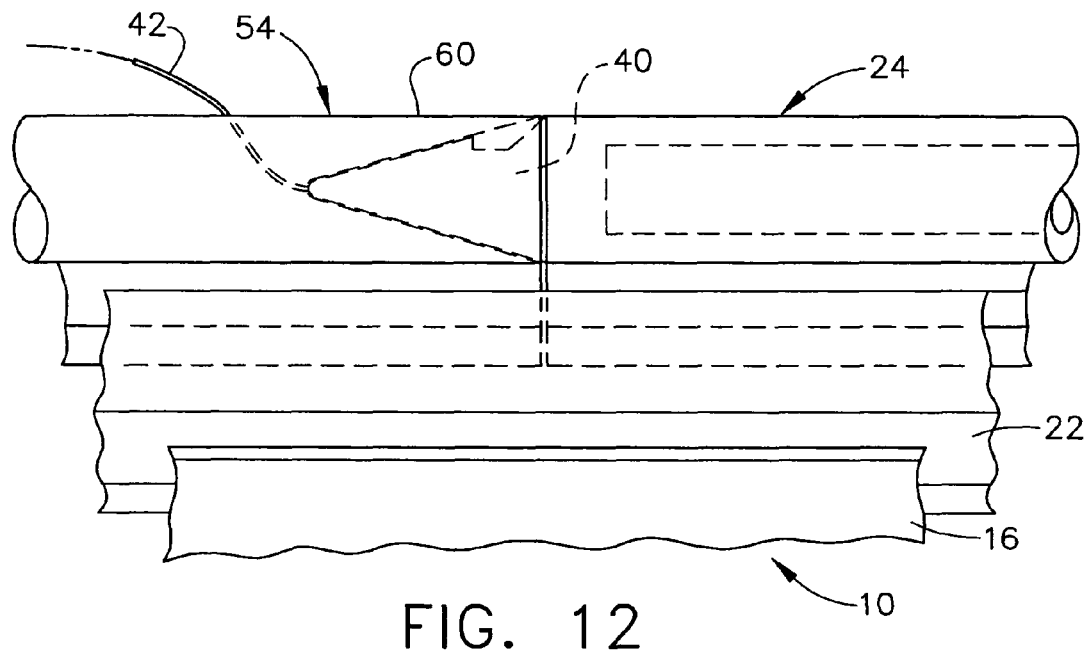
FIG. 12 is a partial, side view of the proximal end of the positioning device of FIG. 10 releasably attached to the distal end of the intubation device shown in FIG. 4, wherein the positioning and intubation devices are slidingly engaged on the carrier, which in turn is slidingly engaged on the track of the guide apparatus.
Figure 13:
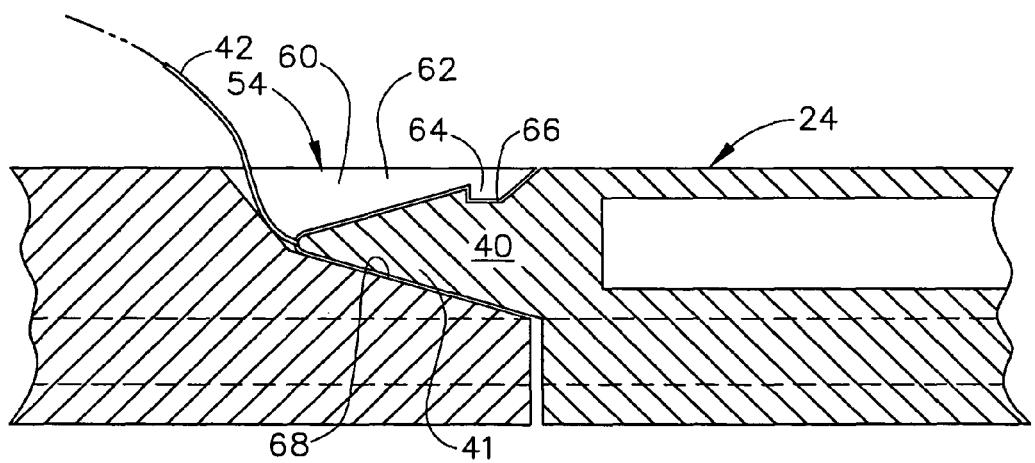
FIG. 13 is a longitudinal sectional view of the proximal end of the positioning device releasably attached to the distal end of the intubation device.

Positioning device 54 may include a coupling member 60 (also referred to as a first coupling member) on the distal end for releasable attachment to coupling member 40 (also referred to as a second coupling member) on the proximal end of intubation device 24. As shown in FIG. 12, the distal end of positioning device 54 may be releasably attached to the proximal end of intubation device 24 while both are slidingly engaged on carrier 22, which in turn is slidingly engaged to track 16 of apparatus 10. FIG. 13 is a longitudinal section of positioning device 54 and intubation device 24 while coupled together. As may be seen in FIGS. 12 and 13, coupling member 60 of positioning device 54 may include a conically shaped receptacle 68 for receiving a conically shaped projection 41 of coupling member 40 of intubation device 24. A latch 64 may be formed in coupling member 60 to engage a strike recess 66 formed into coupling member 40, such that the respective ends of intubation device 24 and positioning device 54 resist being pulled apart until a predetermined separation force is applied. This allows a physician to push and pull on positioning device 54 to position intubation device 24 in the longitudinal direction. The physician may use a snaring device or other type of gripping instrument inserted into a percutaneous incision in the abdominal wall to hold intubation device 24 while pulling on the proximal end extending from the patient's mouth of positioning device 54 to release latch 64 from strike 66 and separate devices 24 and 54. Those having skill in the art will appreciate that the embodiment of coupling members 40 and 60 described herein is merely one example of numerous equivalent embodiments for releasably attaching intubation device 24 and positioning device 54, and that coupling members 40 and 60 may also include a remotely operable release mechanism to separate devices 24 and 54.

As shown in FIGS. 11 and 13, positioning device 54 may also include a slot 62 in the distal end of body 56 to provide clearance for the egress of filament 42 from receptacle 68 when coupling members 40 and 60 are coupled together.

Figure 14:
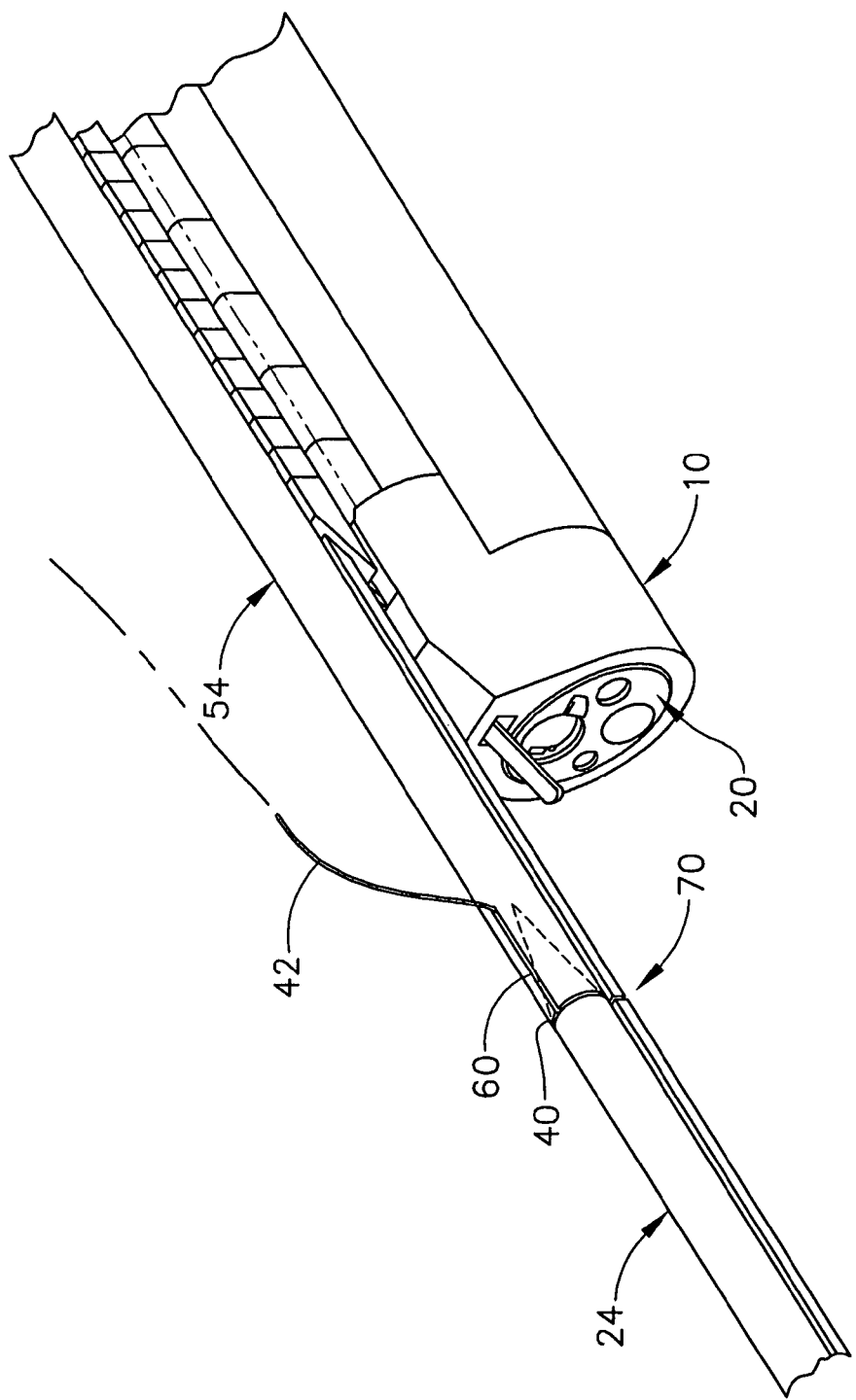
FIG. 14 is a partial, isometric view of the positioning device releasably attached to the intubation device, showing the intubation device advanced to a position distal to the endoscope and the positioning device slidingly engaged on the track of the guide apparatus.

FIG. 14 is an isometric view of the distal portion of guide apparatus 10 assembled onto endoscope 20, showing coupling member 60 of positioning device 54 releasably attached to coupling member 40 of intubation device 24. Intubation device 24, positioning device 54 and guide apparatus 10 may be referred to collectively as an intubation system 70. As shown in FIG. 14, intubation device 24 may be advanced distal to the distal end of endoscope 20, and remain aligned and coupled with positioning device 54. It is possible, therefore to position intubation device 24 further into the small intestine with intubation system 70 than with previous systems due to the ability to releasably attach devices 24 and 54 together. That is, without coupling members 40 and 60, the distal end of positioning device 54 may separate from the proximal end of intubation device 24, and as a consequence, the physician would no longer be able to remotely push or pull intubation device 24 to precisely position the distal end of intubation device 24 in the jejunum, or to hold intubation device 24 stationary relative to the patient while retracting the endoscope and guide apparatus 10. In addition, by being able to move intubation device 24 distal to the distal end of endoscope 20, filament 42 is in an advantageous position for snaring and externalization, as will be further described.

A medical procedure for placing an enteral feeding tube into a patient is known in the art as a PEGJ (percutaneous endoscopic gastrojejunostomy) procedure. This procedure is also sometimes referred to as a JET-PEG (jejunal enteral tube-percutaneous endoscopic gastrostomy) procedure. FIGS. 15-20 illustrate a method of placing intubation device 24 into the small intestine as an alternative to the standard PEGJ procedures (i.e., the Ponsky "Pull" PEG).

Figure 15:
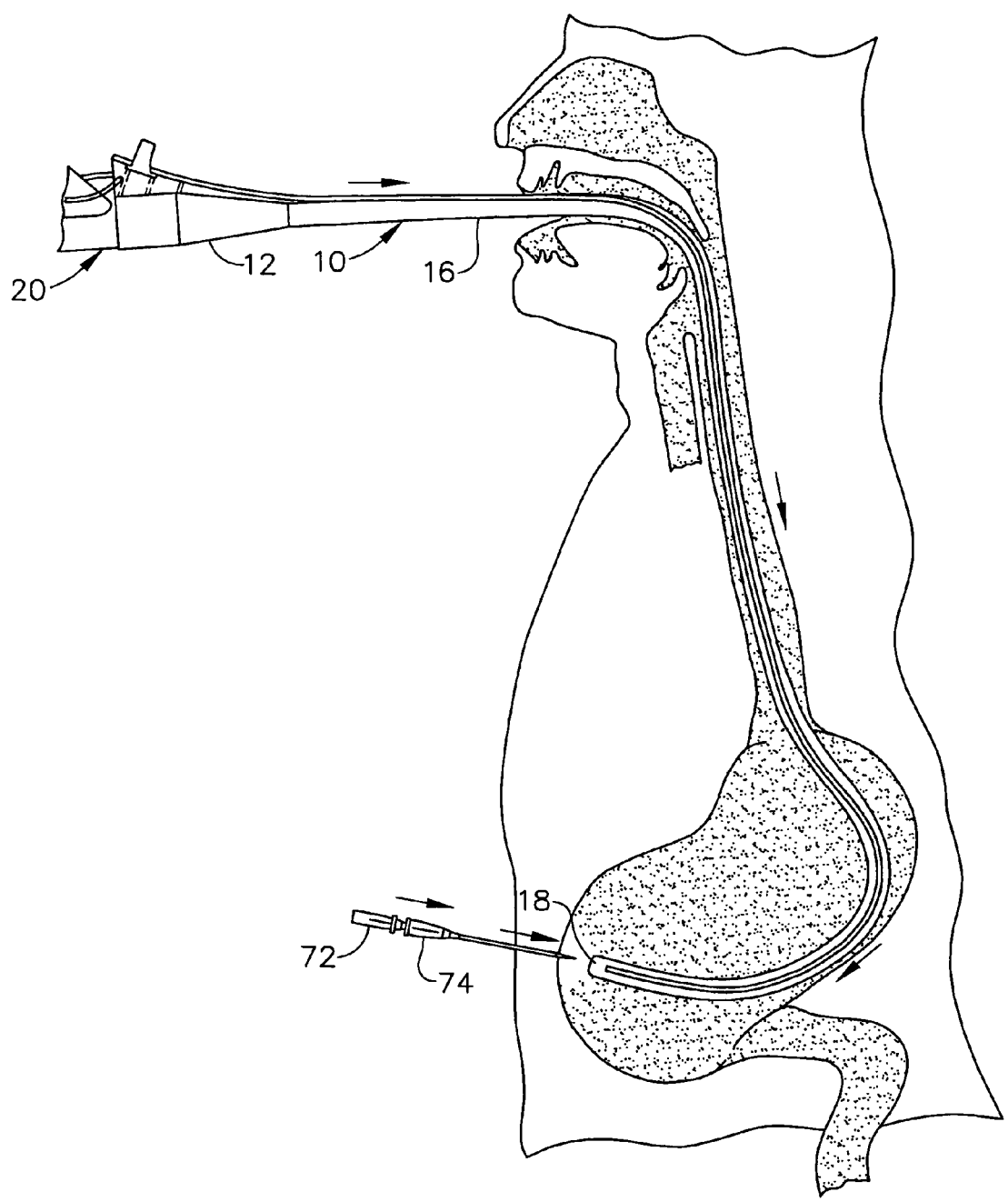

Referring first to FIG. 15, endoscope 20 disposed within guide apparatus 10 comprising handle 12, sheath 16 and endcap 18 may be advanced through the mouth to position the distal end of endoscope 20 and endcap 18 within the stomach of the patient. A light source (such as a light source associated with the distal end of the endoscope) may be employed from within the stomach to transilluminate the abdominal wall, so that the position of the endoscope within the stomach may be observed from outside the patient. A small, percutaneous incision may be made through the abdominal wall, and a needle 72 (such as a 14 gauge needle) and a cannula 74 may be inserted through the incision so that the distal tip of needle 72 and the distal end of cannula 74 may be positioned within the stomach.

Figure 16:
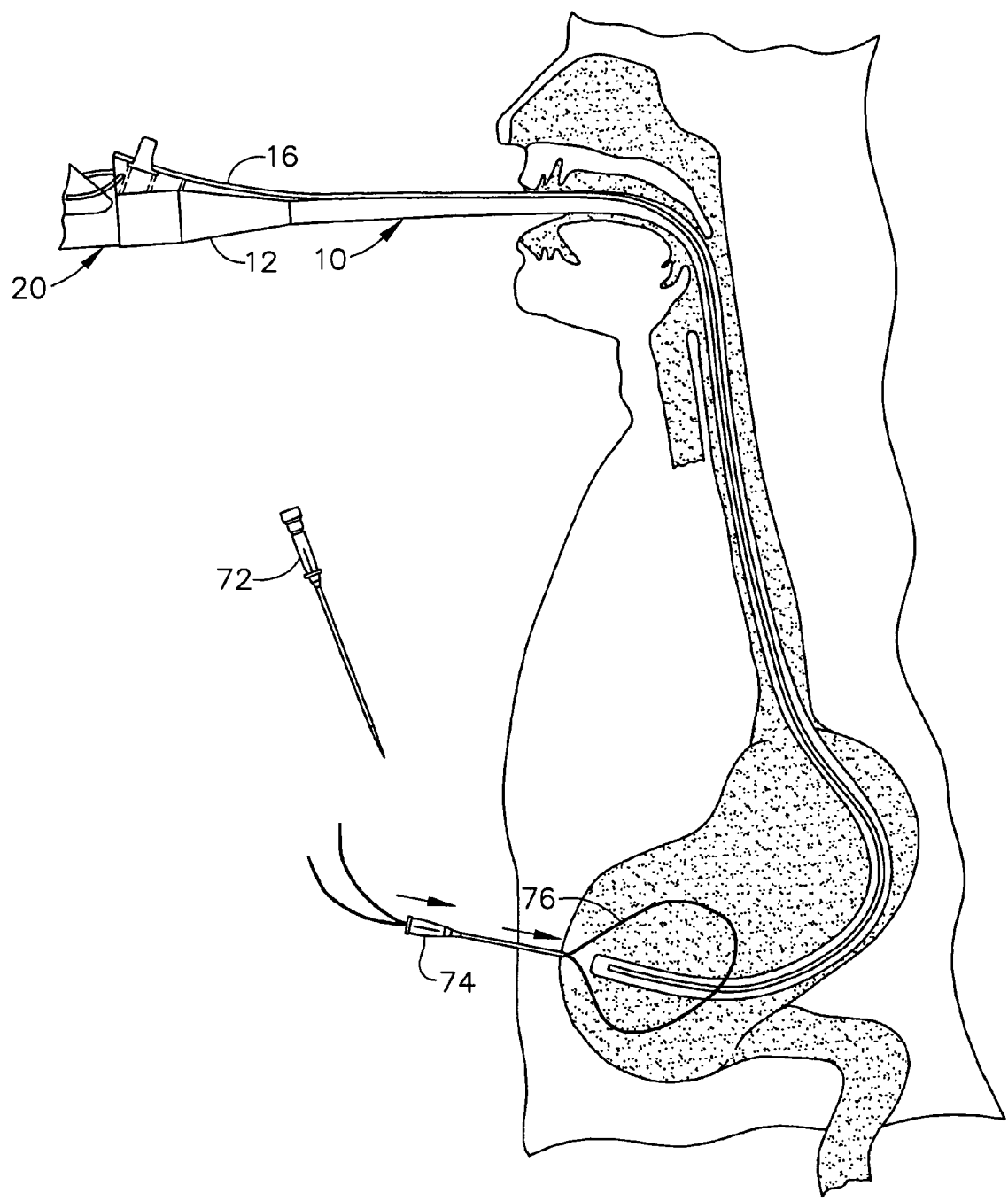

Referring to FIG. 16, needle 72 may be withdrawn, leaving cannula 74 to provide an access channel extending between the inside of the stomach and the outside of the patient. A looped guide wire 76 (also referred to as a wire loop) may be passed through cannula 74, and endoscope 20 and guide apparatus 10 may be directed to extend through the loop provided by guide wire 76. Endoscope 20 and guide apparatus 10 may be advanced distally from the stomach into the small intestine, as shown in FIG. 17.

Figure 17:
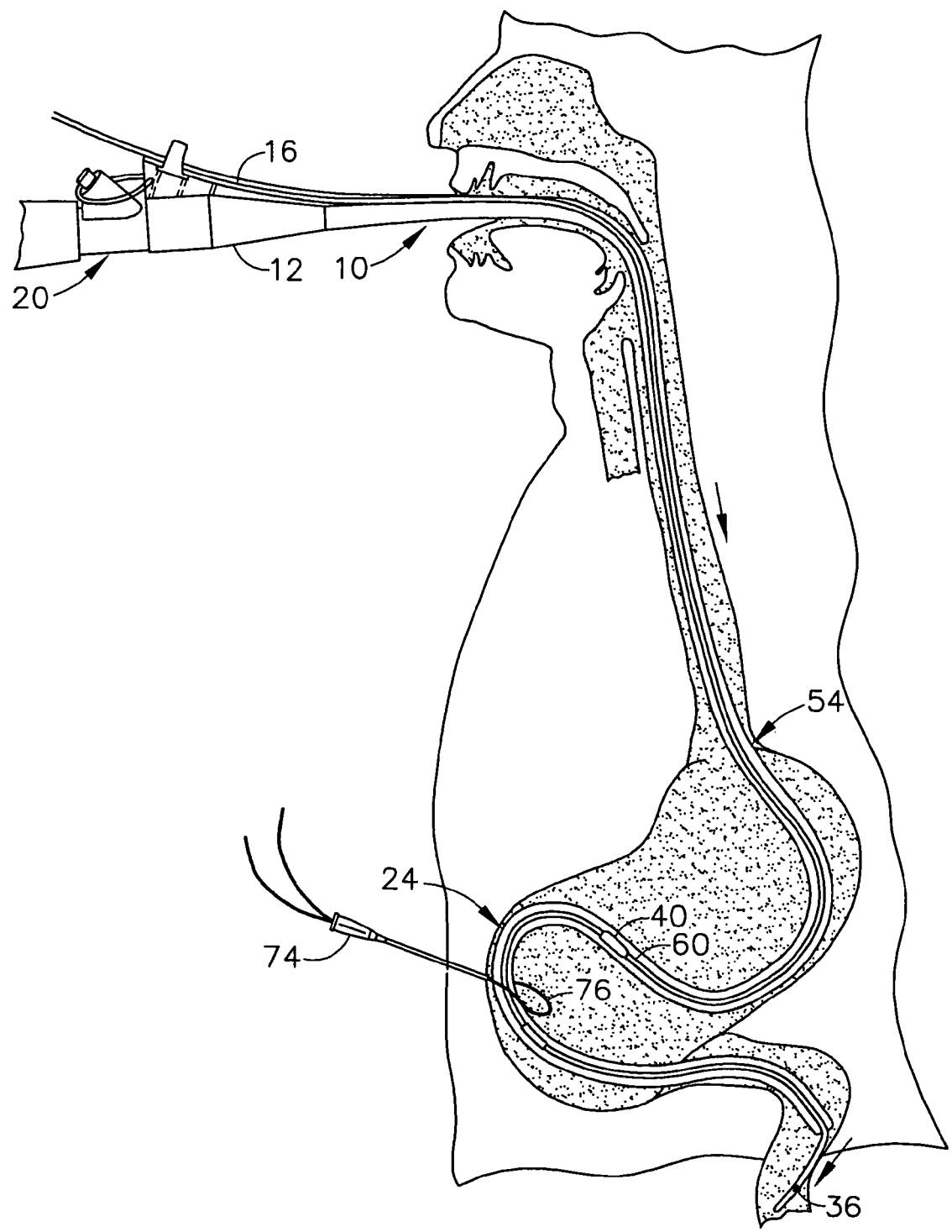

As shown in FIG. 17, positioning device 54 may be releasably attached to intubation device 24 and may be used to advance intubation device 24 along the length of guide apparatus 10 such that intubation device 24 passes through the loop provided by guidewire 76.

Port 36 of intubation device 24 may be advanced in the jejunum, while under visualization of endoscope 20, to a desired position for delivery of nutrients into the GI tract. In one embodiment, intubation device 24 may be positioned on carrier 22 (FIG. 2) outside of the patient's body, and intubation device 24 and carrier 22 may be advanced together along track 16 of guide apparatus 10. In another embodiment, carrier 22 may be engaged to track 16 prior to insertion of endoscope 20 and guide apparatus 10 into the GI tract, and then intubation device 24 and positioning device 54 may be advanced on carrier 22. In a further embodiment, intubation device 24 and positioning device 54 may be engaged to track 16 of guide apparatus prior to insertion of endoscope 20 and guide apparatus 10 into the GI tract. In yet another embodiment, intubation device 24 and positioning device 54 may be engaged into track 16 after endoscope 20 and guide apparatus 10 are inserted into the GI tract.

Figure 18:
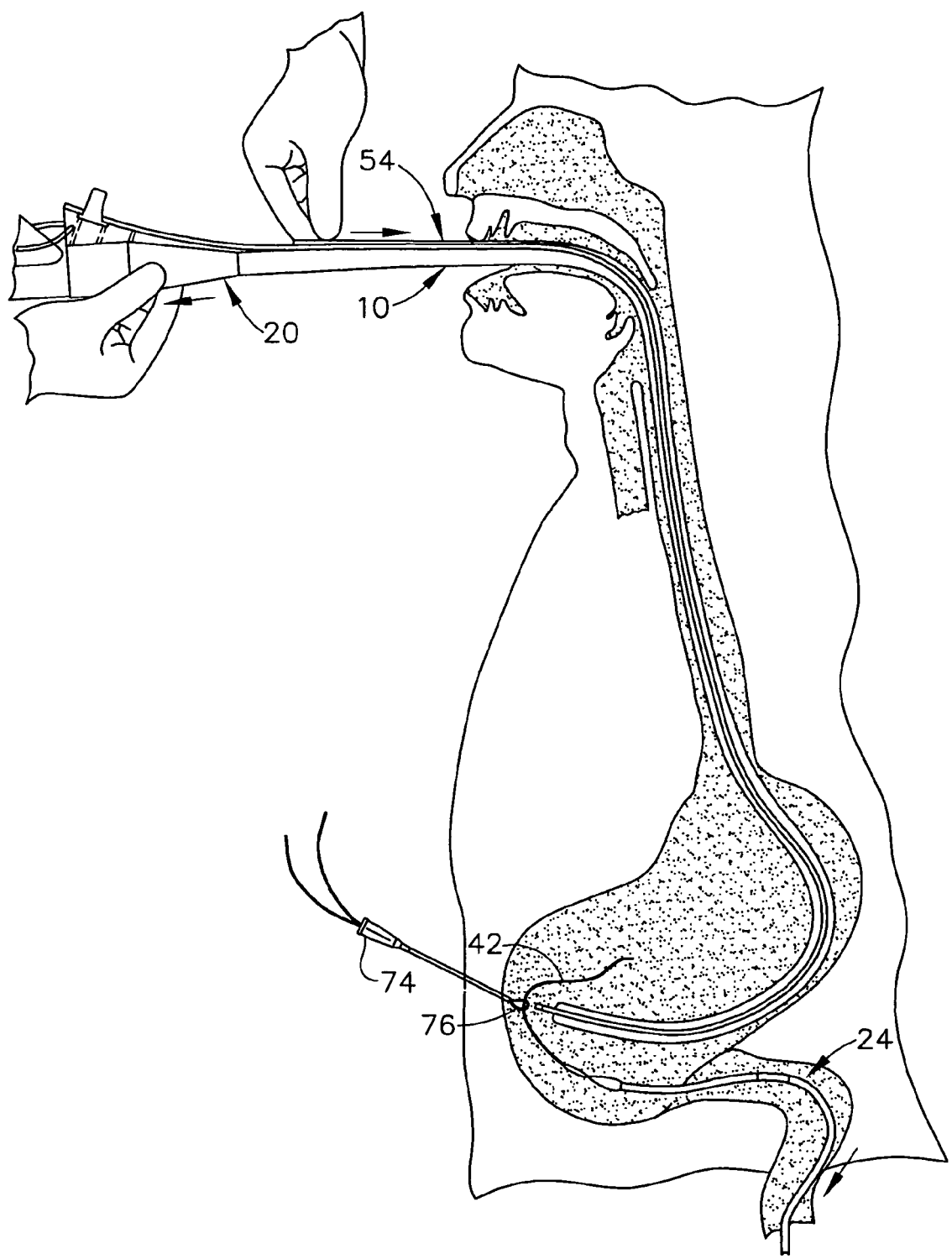

Positioning device 54 may be held in position and endoscope 20 and guide apparatus 10 may be retracted proximally from the stomach, such that intubation device 24 is pushed off the end of guide apparatus 10 by positioning device 54 (as shown in FIG. 14). The physician may close and hold wire loop 76 tightly around the proximal end of intubation device 24 (not shown) and pull back lightly on positioning device 54 to separate first and second coupling members 40, 60. The physician may then slightly loosen and manipulate wire loop 76 to encircle filament 42 extending from the proximal end of intubation device 24, while under visualization of endoscope 20. A length of filament 42 may be snared using the looped guidewire 32, as shown in FIG. 18.

Figure 19:
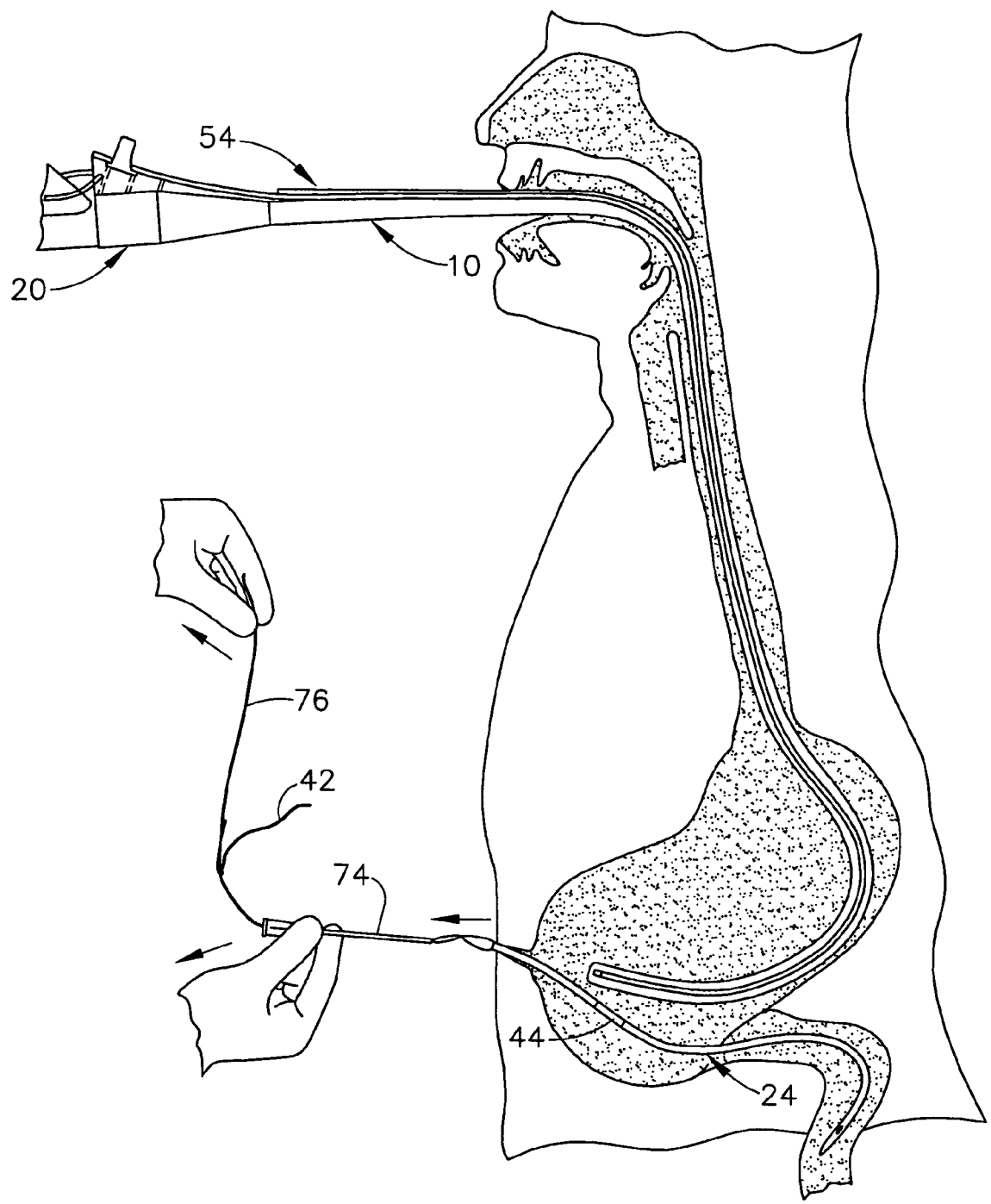

Referring to FIG. 19, filament 42 and the proximal end of intubation device 24 may be pulled through the incision until tissue bolster 44 is positioned against the inner gastric wall with the distal portion of intubation device 24, including port 36 through which nutrients are provided being positioned in the small intestine (such as the jejunum). During the part of the procedure described so far, tissue bolster 44 has been in the collapsed configuration to facilitate insertion and placement of intubation device 24 in the GI tract. When the physician externalizes filament 42 and the proximal end of intubation device 24, and pulls bolster 44 against the inner gastric wall, bolster 44 automatically changes to the expanded configuration.

Figure 20:
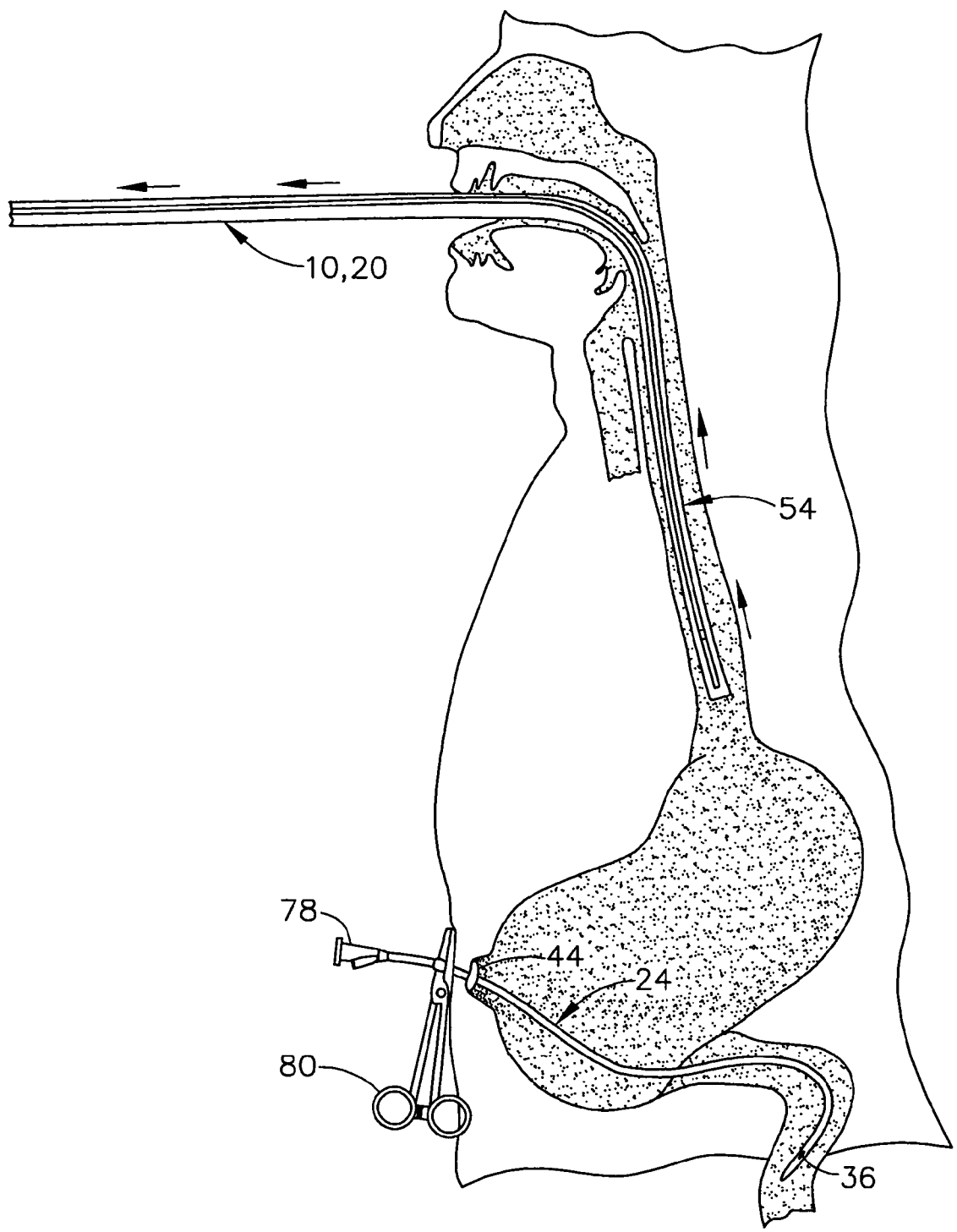

FIG. 20 shows a conventional surgical clamp 80 clamped onto the externalized portion of intubation device 24 against the skin at the incision, thereby holding tissue bolster 44 securely against the inner gastric wall, which in turn bears against the inside of the abdominal wall. Alternately, an external seal (not shown) may be advanced over the proximal portion of intubation device 24 to fit against the patients skin adjacent the incision. The proximal end of intubation device 24 may be cut and a fitting 78 may be attached to the end of intubation device 24 external of the patient. Endoscope 20, guide apparatus 10 and positioning device 54 may be removed from the patient's body, leaving the distal end and port 36 of intubation tube 24 positioned at the desired location within the small intestine.

In the foregoing description, wire loop 76 was used to snare filament 42 and externalize the proximal end of intubation device 24 via cannula 76 through the gastric and abdominal walls. Wire loop 76 may be simply a length of guidewire that is appropriately flexible for passing through a tortuous path in the body, but not necessary optimal for use as a snaring device. That is because the physician often needs to create a loop with the wire that stays open when placed in a body cavity, and that can be manipulated to facilitate insertion of an instrument such as intubation device 24. A conventional guide wire loop introduced through a percutaneous cannula tends to collapse and may be difficult to orient within the body cavity. A physician may prefer to introduce a snaring device through the percutaneous cannula that forms into a relatively stiff loop having a predictable diameter when inside the body cavity, and that may be rotated about the axis of the cannula in order to present the best target to the instrument to be passed through the loop.

Figure 23:
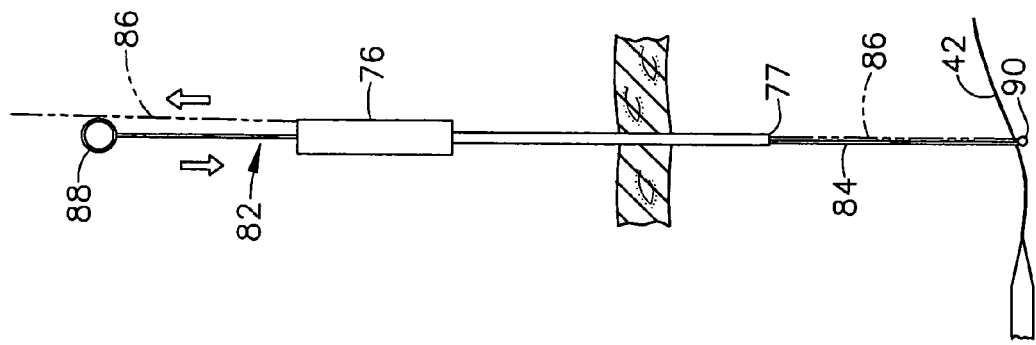
Figure 22:
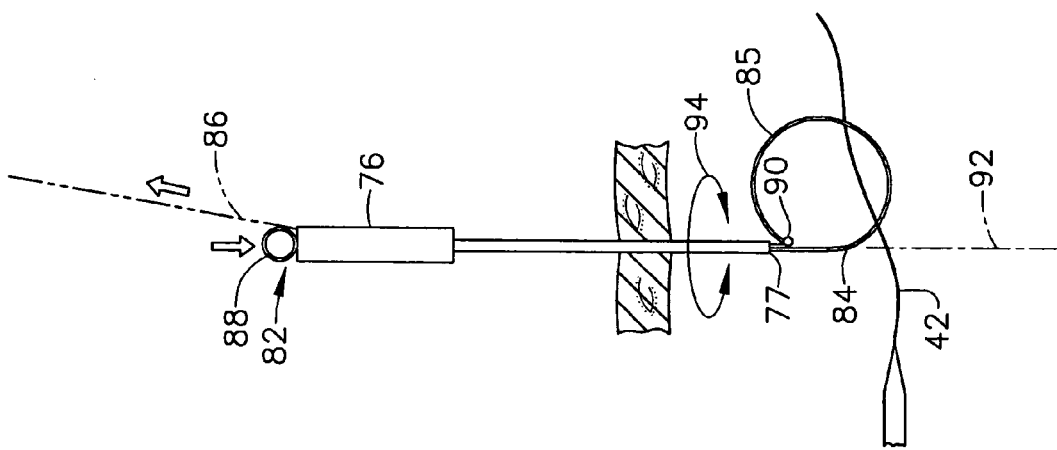
Figure 21:
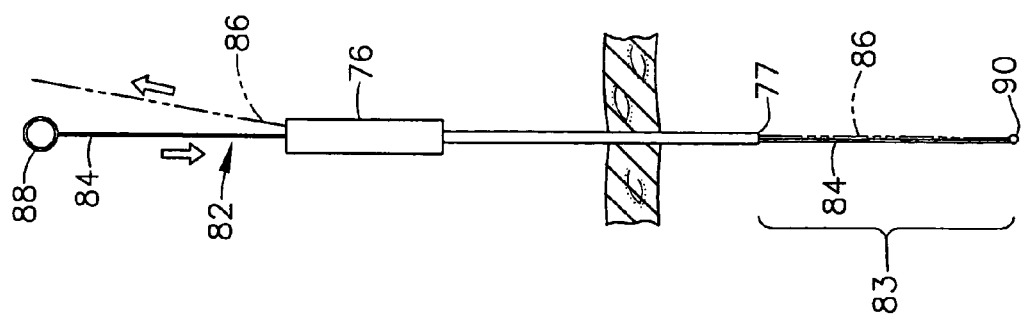

FIGS. 21-23 illustrate an improved snaring device 82 as it may be used with a percutaneous cannula, such as cannula 76 shown in FIGS. 15-19, to snare an instrument or object inside a body cavity of a patient. Snaring device 82 may include an elongated, bendable member 84 formed from a spring material that may be relatively stiff compared to a conventional surgical guidewire. Suitable spring materials include a stainless steel wire, a hardened steel wire with a biocompatible, corrosion resistant surface, a nickel-titanium memory metal wire and a polymeric cord. Bendable member 84 has a first bendable member end 85 and a second bendable member end 83.

Snaring device 82 further includes a control member 94 that may be formed, for example, from a thin wire, a string, a natural fiber, a surgical suture or a filament formed from any one of numerous biocompatible materials. Control member 94 may be flexible or rigid, and may be relatively thin compared to bendable member 84 in order for both to pass easily through cannula 76 when straight and positioned alongside each other. Control member 94 has a first control member end 95 and a second control member end 93.

First control member end 95 may be flexibly connected to first bendable member end 85 by an attachment 96, which may be formed, for example, by gluing, tying, welding, or crimping. Attachment 96 may also be a pivoting, pinned or hinged connection. When a pulling force is applied to second control member end 93 while a pushing force is simultaneously applied to second bendable member end 83, there is no force couple induced in first bendable member end 89.

The length of both bendable member 84 and control member 94 may vary substantially, but a suitable length may be approximately in the range of 20 to 50 centimeters. Snaring device 82 may optionally include a grip 88 attached to second bendable member end 83 for manipulating, holding, and/or applying a force to second bendable member end 83.

Bendable member 84 may be provided in a normally straight configuration or a normally curved configuration. As shown in FIG. 21, a distal portion 98 (shown partially extended from the distal end of cannula 76) of snaring device 82 may be introduced into a body cavity while in a straight configuration. The length of distal portion 98 may be defined as equal to the perimeter of loop 99. As shown in FIG. 22, a pushing force may be applied to second bendable member end 83 and a pulling force may be simultaneously applied to second control member end 93 so that distal portion 98 of bendable member 84 forms into an approximately circular loop 99. The diameter of loop 99 depends on the length of distal portion 98 extending from the distal end 77 of cannula 76. If grip 88 is pushed against the proximal end of cannula 76 as shown in FIG. 22, and the approximate lengths of bendable member 84 and cannula 76 are known, then the approximate length of distal portion 98 and the approximate diameter of loop 99 may be calculated.

Depending on the flexibility of bendable member 84, it is possible, therefore, to form loop 99 when the entire length of distal portion 98 extends into the body cavity before forming loop 99, or when only a very small length of distal portion 98 extends into the body cavity before forming loop 99. In the latter situation, attachment 96 may be only slightly distal to distal end 77 of cannula 76. As the user applies a pushing force to second bendable member end 83, distal portion 98 further extends out of cannula 76 and into the body cavity, forming loop 99. The diameter of loop 99 grows until all of distal portion 98 has been pushed out of cannula 76.

When distal portion 98 is formed into loop 99 as shown in FIG. 22, bendable member 84 may be rotated about an axis 92 of cannula 76 as indicated by arrow 97. Optionally, grip 88 may be keyed to or held firmly against the proximal end of cannula 76 so that cannula 76 and bendable member 84 may be rotated about axis 92 together. In this way, loop 99 may be oriented to provide the optimal target for the instrument or object, such as filament 42, to be passed through loop 98. (As described for FIG. 16, the distal end of the endoscope may be passed through the loop during the PEGJ procedure.) Once the object is encircled, the pushing force applied to second bendable member end 83 and the pulling force applied to second control member end 94 may be removed such that distal portion 98 springs back to the straight configuration, as shown in FIG. 23. Snaring device 82 may then be withdrawn from cannula 76, thereby externalizing at least a portion of the snared object (filament 42.)

Figure 24:
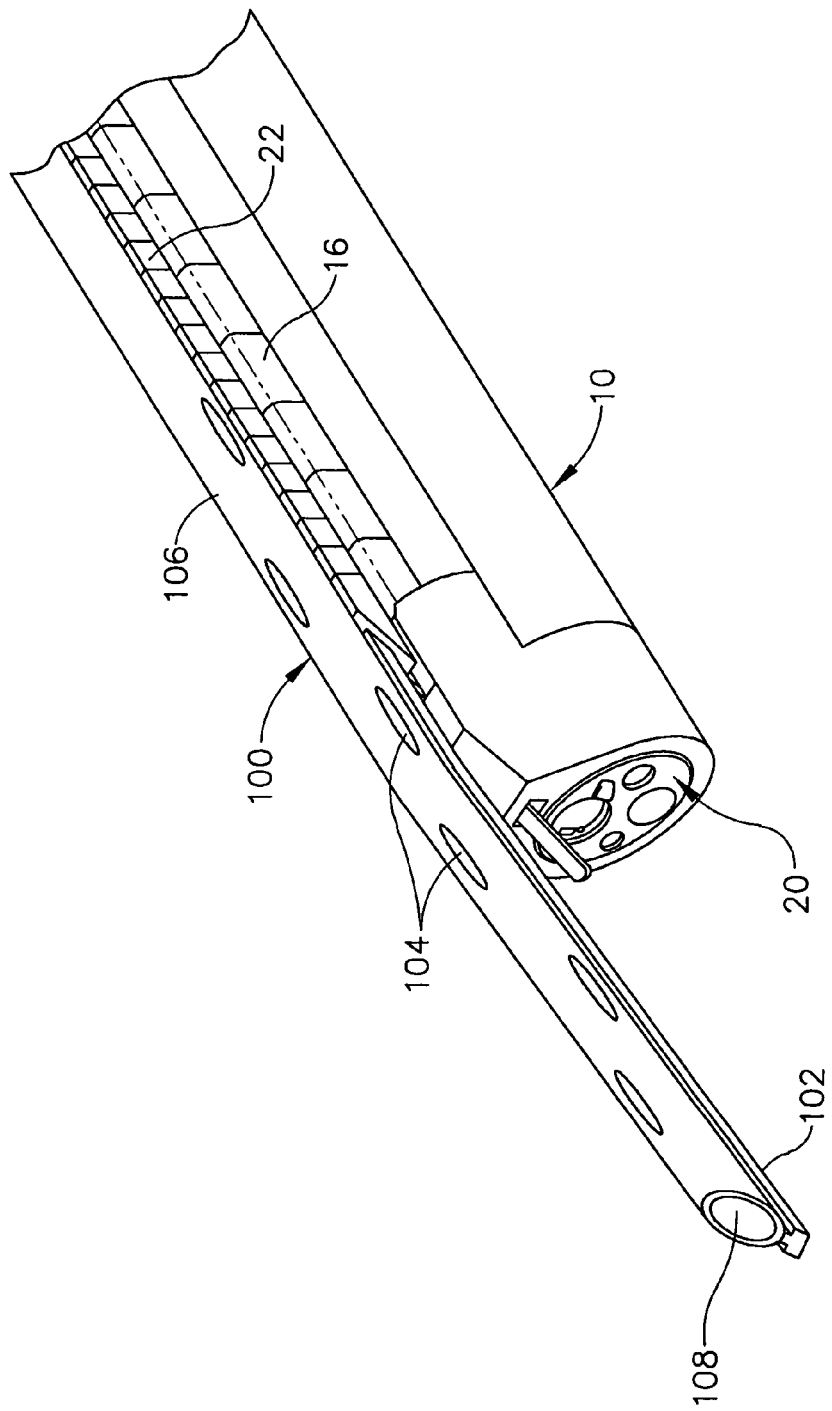
FIG. 24 is an isometric view of the distal portion of another example of an intubation device, which is slidingly engaged on the guide apparatus of FIG. 2.

FIG. 24 is an isometric view of the distal portion of endoscope 20, guide apparatus 10 and another example of an intubation device, generally designated 100, for use with guide apparatus 10. Intubation device 100, also be referred to as a colonic decompression tube, may be used primarily for the evacuation of fluid such as a gas from the colon of a patient. Intubation device 100 may include an elongated tube 106 defining a channel 108 therethrough. Intubation device 100 also includes a flexible rail 102 (also referred to as a mating part) attached to or unitarily formed with tube 106 along a portion or substantially the entire length of tube 106. Tube 106 and rail 102 may be formed from an extruded polymer such as polyurethane, and have a similar cross-sectional profile as intubation device 24 shown in FIG. 3, although many other shapes are possible. Like intubation device 24, intubation device 100 may be adapted to be slidingly engaged with carrier 22 or track 16 of guide apparatus 10.

Intubation device 100 may include a plurality of spaced-apart apertures 104 in at least the distal portion of tube 106 and in fluid communication with channel 108. The size and shape of apertures 104 may vary significantly, but may be generally large enough for the release of gas from the colon. The distal end of intubation device 100 may be tapered as shown in FIG. 24 to facilitate atraumatic insertion into the colon. The proximal end of intubation device 100 (not shown) may simply be a cut end or may be adapted for connection to a fluid collection system (not shown). The length of intubation device 100 may be at least as long to extend from the patient's anus to the cecum of the colon, plus an additional length to extend externally from the patient for proper management of the released or evacuated fluid. For example, the length of intubation device may be approximately in the range of 100 to 200 centimeters.

Figure 25:
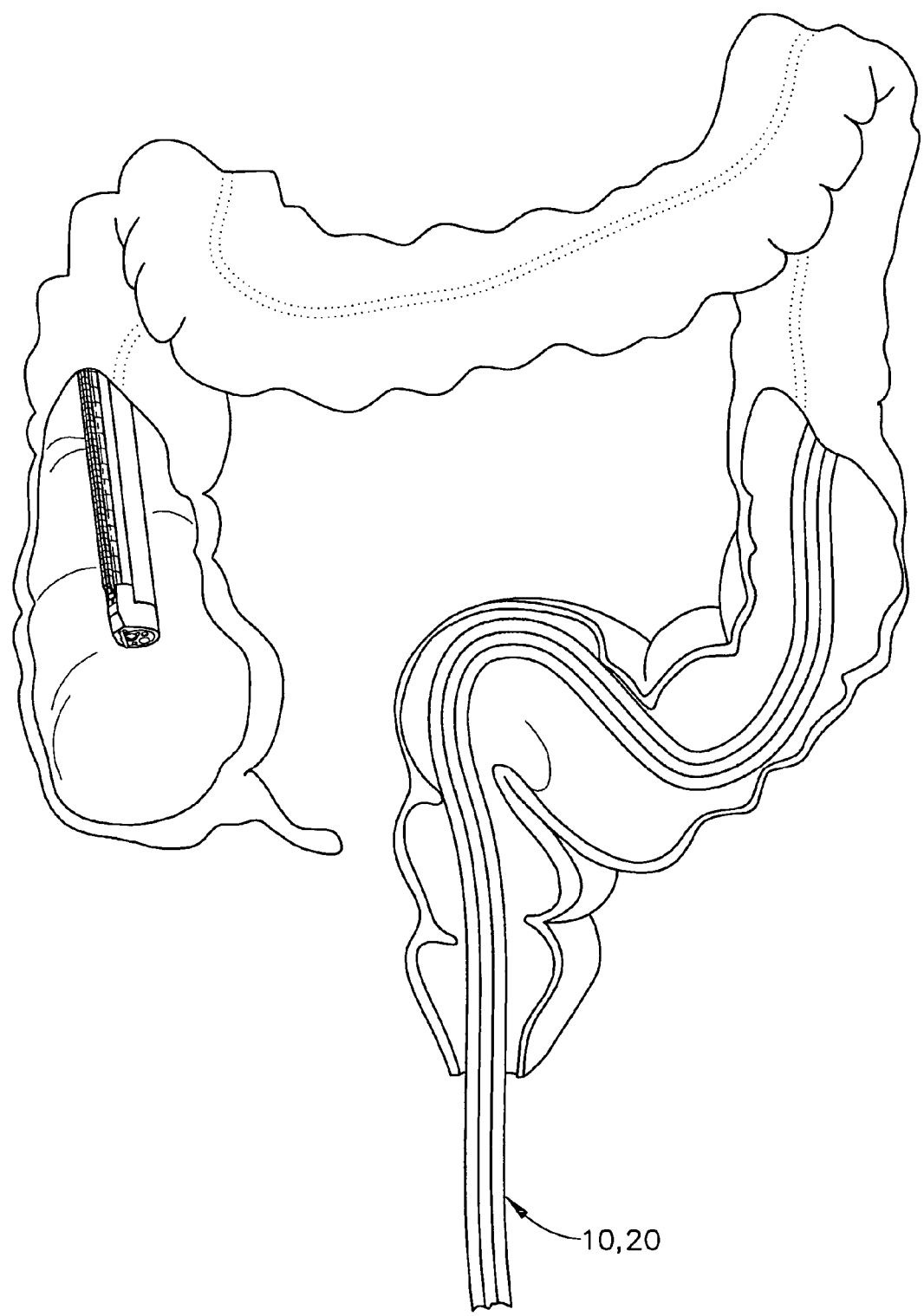
FIG. 25 illustrates the guide apparatus of FIG. 2 assembled onto an endoscope and inserted through the anus into the colon of a patient.
Figure 26:
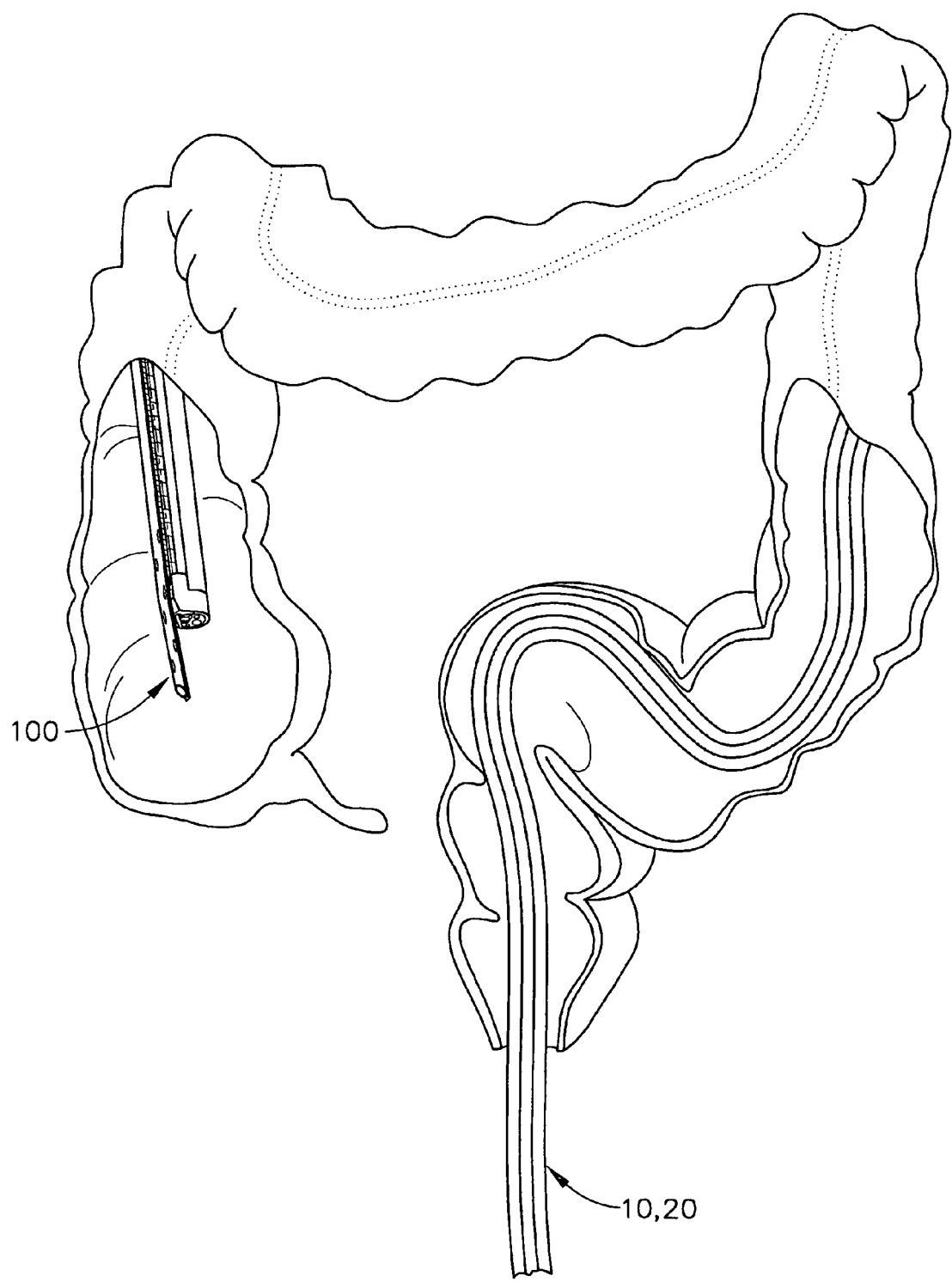
FIG. 26 illustrates the intubation device of FIG. 24 advanced along the guide apparatus into the colon of the patient.
Figure 27:
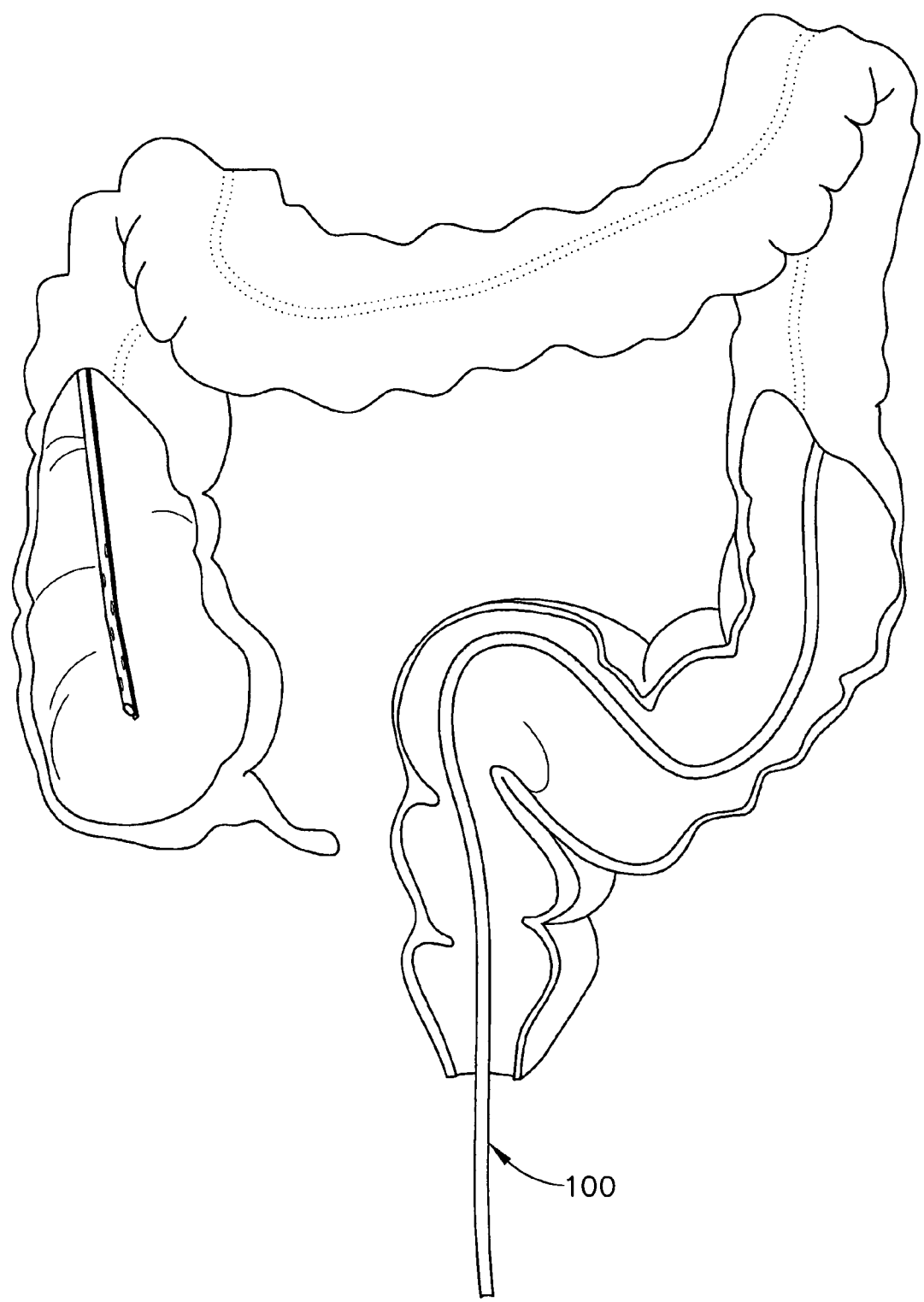
FIG. 27 illustrates the intubation device of FIG. 24 positioned in the colon of the patient and the endoscope removed from the patient.

FIGS. 25-27 illustrate a method of placing intubation device 100 into the colon of a patient, using guide apparatus 10 with an endoscope, in order to release and/or evacuate fluid from the colon. Endoscope 20 may be provided with guide apparatus 10 of FIG. 1 attached thereto, and may be inserted through the anus into the colon. As shown in FIG. 25, endoscope 20 and guide apparatus 10 may be inserted until the distal end of endoscope 20 extends into the desired region within the colon, such as in the cecum of the colon.

Intubation device 100 may be advanced along guide apparatus 10 until the distal end of intubation device 100 is at the desired location within the colon, as shown in FIG. 26. Optionally, intubation device 100 may be slidingly engaged with guide apparatus 10 before insertion of endoscope 20 into the colon. The distal end of intubation device 100 may be near the distal end of endoscope 20 prior to insertion, or at any location proximal to the distal end of endoscope 20.

Endoscope 20 and guide apparatus 10 may be retracted from the colon while the proximal end of intubation device 100 is held stationary relative to the patient, thereby keeping the distal end of intubation device 100 at the desired location within the colon, as shown in FIG. 27. The proximal end of intubation device 100 may be positioned for the natural release of gas or connected to a fluid collection system.

Although an intubation system and method has been shown and described with respect to certain aspects, variations, and embodiments, it should be understood that modifications may occur to those skilled in the art.

What is claimed is:

1. A medical intubation system comprising:
   an elongated track having a first length;
   an intubation device slidably engaged with said elongated track, said intubation device including a first coupling member disposed on a proximal end of said intubation device; and
   an elongated positioning device slidably engaged with said elongated track, said positioning device having a second length and including a second coupling member disposed on a distal end of said positioning device, wherein said second length is greater than said first length,
   wherein said first coupling member is engaged with said second coupling member to releasably connect said intubation device to said positioning device.

2. The medical intubation system of claim 1 wherein said elongated track is positioned on a guide apparatus adapted to receive an endoscope therein.

3. The medical intubation system of claim 1 wherein said first and said second coupling members are adapted to be releasably attached and then separated while inside a patient's body.

4. The medical intubation system of claim 1 wherein said first coupling member may be disengaged from said second coupling member by applying a separation force, thereby disconnecting said intubation device from said positioning device.

5. The medical intubation system of claim 1 wherein said first coupling member includes a conically shaped projection and said second coupling member includes a conically shaped receptacle adapted to receive said conically shaped projection.

6. The medical intubation system of claim 1 wherein said first coupling member includes a strike recess and said second coupling member a latch adapted to engage said strike recess.

7. The medical intubation system of claim 1 wherein said intubation device and said first coupling member are unitarily formed.

8. The medical intubation system of claim 1 wherein said positioning device and said second coupling member are unitarily formed.

9. The medical intubation system of claim 1 wherein at least one of said intubation device and said positioning device is formed from a polymeric material.

10. The medical intubation system of claim 1 wherein said intubation device includes a channel extending therethrough.

11. The medical intubation system of claim 1 wherein said intubation device includes a trailing filament connected to said proximal end of said intubation device.

12. The medical intubation system of claim 11 wherein said trailing filament includes at least one of a surgical suture material, a polymeric cord, a metallic wire, a string and a natural fiber.

13. The medical intubation system of claim 1 wherein said positioning device includes a channel extending therethrough.

14. The medical intubation system of claim 1 wherein said intubation device includes a generally T-shaped rail adapted to engage said track.

15. The medical intubation system of claim 14 wherein said track include a generally C-shape channel adapted to receive said generally T-shaped rail.

16. The medical intubation system of claim 1 further comprising a carrier disposed between said intubation device and said track.

17. The medical intubation system of claim 1 wherein said positioning device has a length of at least 100 centimeters.

* * * * *